(12) United States Patent
Poirot et al.

(10) Patent No.: US 7,947,668 B2
(45) Date of Patent: May 24, 2011

(54) AMINOALKYL STEROL COMPOUNDS HAVING AN ANTI-TUMORAL AND NEUROPROTECTIVE ACTIVITY

(75) Inventors: Marc Poirot, L'Union (FR); Philippe De Medina, Balma (FR); Sandrine Poirot, L'Union (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 1141 days.

(21) Appl. No.: 10/511,765

(22) PCT Filed: Apr. 18, 2003

(86) PCT No.: PCT/FR03/01248
§ 371 (c)(1),
(2), (4) Date: May 5, 2005

(87) PCT Pub. No.: WO03/089449
PCT Pub. Date: Oct. 30, 2003

(65) Prior Publication Data
US 2005/0222097 A1    Oct. 6, 2005

(30) Foreign Application Priority Data
Apr. 19, 2002 (FR) ..................... 02 04912

(51) Int. Cl.
*A61K 31/575* (2006.01)
*A61K 31/58* (2006.01)
*C07J 41/00* (2006.01)
*C07J 43/00* (2006.01)

(52) U.S. Cl. ......... 514/176; 514/182; 540/108; 552/515

(58) Field of Classification Search ............... 552/515, 552/540; 514/182
See application file for complete search history.

(56) References Cited

FOREIGN PATENT DOCUMENTS
| FR | 2047880 | 6/1969 |
| FR | 2 047 880 | 3/1971 |
| WO | 86/03299 | 6/1986 |
| WO | 97/10836 | 3/1997 |

OTHER PUBLICATIONS

El Kihel et al., "Synthesis and cytotoxicity of aminosterols: Activity studies on a non-small-cell bronchopulmonary carcinoma line (NSCLC-N6)." Anticancer Research, vol. 19, pp. 1229-1234, 1999.*
Pinhas et al., "6-Amino derivatives of stigmastanol and cholestanol," *J. Med. Chem.* (1971), 14(11), 1048-0 XP002220449, p. 1048-9.
Elkihel et al., "Synthesis of aminocholesterol derivatives with antibiotic properties", *Synthetic Communications*, (1997), 27(11), XP008010386 pp. 1951-1962.
Elkihel, L. et al., "Synthesis and preliminary in vitro evaluation of antitumor nitrosoureido cholesterol derivatives", *Arzneimittel-Forschung*, (1995), 45(2), XP-002220450, pp. 190-194.
Shafiullah et al., "Syntheses of steroidal substituted tetrazoles", *ACTA Chimica Hungarica*, vol. 127, No. 3, 1990, XP008010474 pp. 391-394.
El Kihel, L. et al., Synthesis and cytotoxicity of aminosterols: Activity studies on a non-small-cell bronchopulmonary carcinoma line (NSCLC-N6), *Anticancer Research*, (1999), 19(2A), XP008010475, pp. 1229-1234.
Suh, N. et al., A novel synthetic oleanane triterpenoid, 2-cyano-3, 12-dioxoolean-1, 9-dien-28-oic acid, with potent differentiating, antiproliferative, and anti-inflammatory activity, *Cancer Research*, United States Jan. 15, 1999, vol. 59, No. 2, XP-002220453, pp. 336-341.

* cited by examiner

*Primary Examiner* — Barbara P Badio
(74) *Attorney, Agent, or Firm* — Young & Thompson

(57) ABSTRACT

Sterol derivatives of formula (I) and a method for the production of the compounds, a medicament using one of the compounds and a pharmaceutical composition comprising the medicament.

8 Claims, 9 Drawing Sheets

Control — Test compound

Control — Test compound

AMINOALKYL STEROL COMPOUNDS HAVING AN ANTI-TUMORAL AND NEUROPROTECTIVE ACTIVITY

BACKGROUND OF THE INVENTION

1. Field of the Invention

The invention relates to novel sterol derivatives, to a novel process for obtaining these compounds and to the use of said compounds for the production of secretory vacuoles in tumoral cells, especially for the regression of cancer tumors, to increase dendritogenesis and to combat neurodegenerative diseases and for activation of the immune system.

2. Description of Related Art

Dendritogenesis is a morphological change in cells that takes place especially in the nervous system and in the immune system. In the immune system, dendritogenesis leads to the generation of dendritic cells from monocytes. These physiologically important phenomena are not very well understood at the present time, but they are associated with an increase in the secretory activity of the cells (Martinez-Arca S. et al., 2001, J. Neurosci, 21 (11), 3830-38 and Denzer K et al., 2000, J. Cell. Sci., 113 Pt 19, 3365-74). These phenomena are induced by growth factors and cytokines. The differentiation of monocytes into dendritic cells (CD) is induced by cotreating monocytes with interleukin-4 (IL4/GM-CSF), the activation of the CDs also requiring a treatment with TNF-α (tumor necrosis factor alpha).

It is known that tumoral cells are antigenic and express at their surface antigens that are specifically recognized by lymphocytes. These antigens are peptides charged on the class I CMH molecules: a specific CD8− T lymphocyte recognizes this CMH-peptide complex. It has been shown that CDs modified ex vivo to exhibit tumoral antigens induced a specific immunity preventing and/or eradicating tumors established in mice. (Schuler P. Steinman R M, J. Exp. Med. 1997, 8, 1183-7 and Angevin, André, Zitvogel, Bull Cancer, 2000, 87(1), 107-15). It has thus been considered that CDs are potent adjuvants for inducing a therapeutic immune response.

At the present time, cellular therapy thus concerns methods for the ex vivo generation of human CDs for clinical use.

In the case especially of breast cancer, it has already been proposed to remove monocytes from the patient and to culture them in the presence of a combination of cytokines and of the antigen to be presented; the dendritic cells obtained by dendritogenesis were reinjected into the patients to develop the cytotoxic T lymphocytes specific for the antigen (Lawrence Fong and Edgar G. Engleman, Annu. Rev. Immunol., 2000, 18, 245-273).

The prior art that has just been described demonstrates the drawbacks inherent in these methods. Specifically, sensitization of the dendritic cells uses peptides derived from tumoral antigens; however, for the majority of tumors, the specific antigens have not been identified. Furthermore, to sensitize the dendritic cells, use is generally made of peptides identified in the tumoral cells by means of cytotoxic T lymphocyte clones specific for the tumor; however, the epitopes presented by the tumoral cells and those presented by the antigen-exhibiting dendritic cells are probably not the same. What is more, when dendritic cells that have been subjected to the various ex-vivo treatments described above are used, phenotypic changes may take place leading to heterogeneous cell populations that are unsuitable for therapeutic use. It is thus highly desirable to improve the methods for obtaining sensitized dendritic cells, in order to enable the development of immunotherapy.

BRIEF SUMMARY OF THE INVENTION

The invention is based on the fact that it has been found that, entirely surprisingly, the differentiation of monocytes into dendritic cells can be induced in vivo by means of a class of novel sterol-based compounds. Hitherto, the use of non-peptide compounds was envisioned only for potentiating neuritogenesis (Pradines and coworkers, 1995, J. Neurochem., 64, 1954-64); there was nothing to suggest to a person skilled in the art that non-peptide molecules were capable of inducing the differentiation of monocytes into dendritic cells. According to the invention, and entirely surprisingly, it has been found that one category of sterols mimics, at low dose, the dendritogenic growth factor effect and the cytokine effect.

BRIEF DESCRIPTION OF THE DRAWINGS

FIG. 11.1 shows the "control" cells (magnification: 6000); FIG. 11.2 shows the cells treated with the test compound (magnification: 4000); FIG. 11.3 shows a magnification of the vesicles that can be seen in FIG. 11.2 (magnification: 25 000); FIG. 11.4 shows a detail of the content of an intracytoplasmic vacuole (magnification: 72 000). The letters used in FIG. 11 have the following meanings: N=nucleus; C=cytoplasm; M=mitochondria; Vi=intracytoplasmic vesicles; Ve=extracellular vesicles; MLB=multilamellar body.

DETAILED DESCRIPTION OF THE INVENTION

Figure 1:
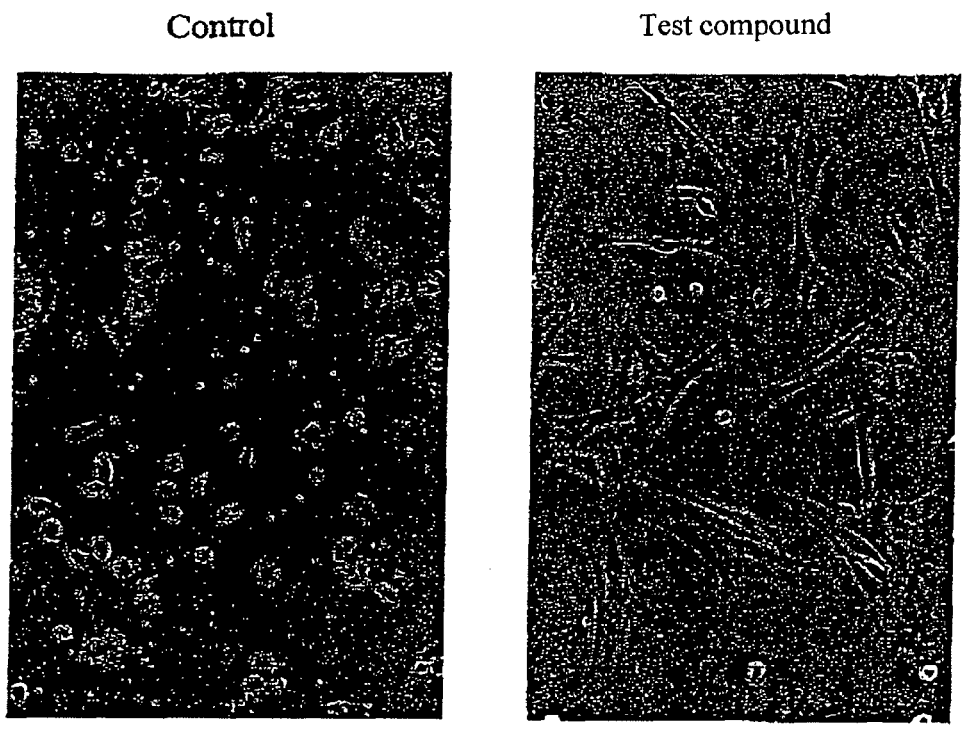
FIG. 1 shows the major morphological changes on the mouse monocytes (control) obtained using compound cholestane-3β,5α-diol-6β-N-[2-ethylamino(1H-imidazol-4-yl)] of example 9, the conversion resulting in dendritic cells (test compound).

A first subject of the present invention is, consequently, novel sterol derivatives capable of affording the effect indicated above. These derivatives are the compounds of formula (I):

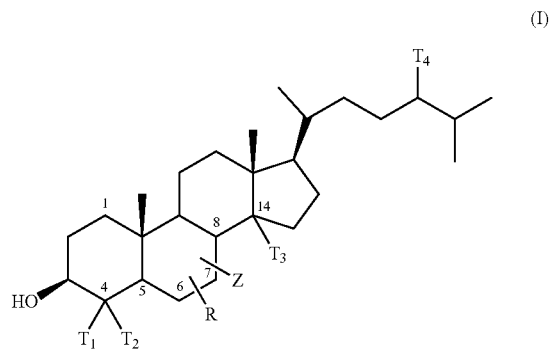

(I)

in which formula the carbon in position 4 of the cholesterol skeleton bears moieties $T_1$ and $T_2$, which may be, independently, H or $CH_3$ with $CH_3$ in the α and/or β position, the carbon in position 24 bears a moiety $T_4$ which represents H, $CH_3$ or $C_2H_5$, the carbon in position 14 bears a moiety $T_3$, which may be H or a β $CH_3$, one of the bonds between carbons 5 and 6, on the one hand, and 7 and 8, on the other hand, may be a double bond, whereas the other is a single bond, and in which:

Z represents, in position 5 or 8, either H or OH, OH being able to be borne only by a carbon that does not bear a double bond; and R represents in position 6 or 7, on a carbon not bearing a double bond, the substituent of formula $-Q_0-Q_1$, in the formula of which substituent $-Q_0-$ represents the radical of formula (II):

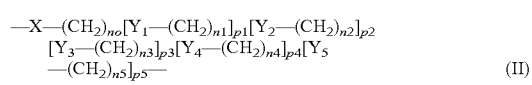

(II)

in which formula (II):

p1, p2, p3, p4 and p5 are integers independently equal to 0 or 1, n0, n1, n2, n3, n4 and n5 are independent integers such that:
$1 \leq n0 \leq 4$
$0 \leq n1, n2, n3, n4, n5 \leq 4$ —X— represents —S—, —O—, —CH$_2$— or —NR$_3$—, in which R$_3$ is H or a C$_1$-C$_4$ alkyl radical, or alternatively a heterocycle

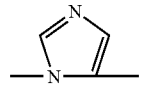

—Y$_1$—, —Y$_2$—, —Y$_3$—, —Y$_4$— and —Y$_5$— represent, independently of each other, —S—, —O—, —C— or —NR$_3$—, in which R$_3$ has the meaning given above;

and in which formula
Q$_1$ represents an indole nucleus, a morpholine or thiomorpholine nucleus attached via its nitrogen atom, a heterocycle

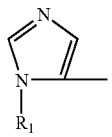

in which R$_1$ represents H, COCH$_3$, a C$_1$-C$_4$ alkyl radical, or

in which R$_1$ has the meanings given above and R$_2$ represents H or a C$_1$-C$_4$ alkyl radical, R$_1$ and R$_2$ together possibly constituting a piperidine, pyridine or piperazine ring optionally substituted with a C$_1$-C$_4$ alkyl radical, or alternatively a pyrrole or pyrrolidine heterocycle comprising a nitrogen atom and 4 carbon atoms, with the proviso that:

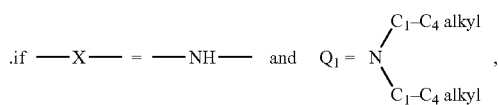

at least one of the numbers p1, p2, p3, p4 and p5 is other than 0; and if —X—=—CH$_2$—, n0=1 and all the numbers p1, p2, p3, p4 and p5 are zero, Q$_1$ is other than —NH$_2$.

A subject of the present invention is also a process for obtaining the compounds of formula (I), in which:

in a first step, meta-chloroperoxybenzoic acid, dissolved in a solvent A, is reacted with a compound corresponding to formula (III)

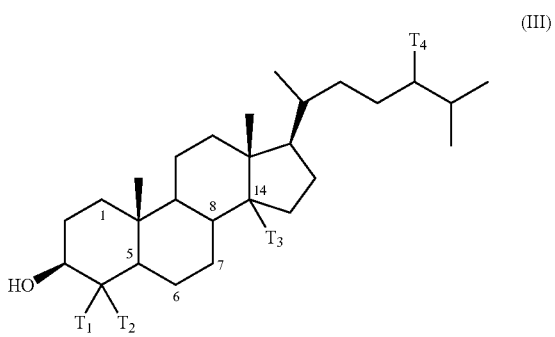

in which formula the carbon in position 4 of the cholesterol skeleton bears moieties T$_1$ and T$_2$ which may be, independently, H or CH$_3$ with CH$_3$ in the α and/or β position, the carbon in position 24 bears a moiety T$_4$ that represents H, CH$_3$ or C$_2$H$_5$, the carbon in position 14 bears a moiety T$_3$, which may be H or a β CH$_3$, at least one of the bonds between carbons 5 and 6, on the one hand, and 7 and 8, on the other hand, is a double bond, the compound of formula III being dissolved in a solvent B that is miscible with solvent A, in a second step, the epoxy compound obtained in the first step, dissolved in a solvent C in the presence of an activator D, is reacted with an amine of formula Q$_0$Q$_1$, Q$_0$ and Q$_1$ having the meanings given in claim 1, dissolved in a solvent E that is miscible with the solvent C.

Among the preferred compounds of formula (I), mention should be made of:

cholestane-3β,5α-diol-6β-N-[1-N1-(3-aminopropyl)butane-1,4-diamine];

cholestane-3β,5α-diol-6β-N-[N,N'-bis(3-aminopropyl)butane-1,4-diamine];

cholest-7-ene-3β,5α-diol-6β-N-[1-N1-(3-aminopropyl)butane-1,4-diamine];

cholest-7-ene-3β,5α-diol-6β-N-[N,N'-bis(3-aminopropyl)-butane-1,4-diamine];

cholest-7-ene-3β,5α-diol-6β-N-[2-ethylamino(3H-imidazol-4-yl)];

cholestane-3β,5α-diol-6β-N-[2-ethylamino(3H-imidazol-4-yl)];

cholest-7-ene-3β,5α-diol-6β-N-(4-aminobutylamine);

cholest-7-ene-3β,5α-diol-6β-N-{2-[2-(2-aminoethoxy)-ethoxy]ethylamine};

cholestane-3β,5α-diol-6β-N-[4-(2-aminoethyl)imidazol-1-yl];

cholestane-3β,5α-diol-6β-N-({1H-imidazol-4-yl}ethyl)-acetamide.

It has especially been found that the use of the compounds of formula (I) at nanomolar doses induces the production of secretory vacuoles in various tumoral cell lines, which, according to the prior art, is generally associated with dendritogenesis, and in immortalized cell lines such as NIH-3T3 or COS-7.

A subject of the invention is thus also a medicament, characterized in that it comprises, in a pharmaceutically acceptable vehicle, at least one compound of formula (I).

In a first variant, the medicament defined above is used to increase the dendritogenesis of living mammalian cells; it may be used to trigger neuritogenesis on nerve cells or precursors thereof and to combat human neurodegenerative diseases.

In another variant, the medicament defined above is used to activate the immune system of a live organism.

In a third variant, the medicament defined above is used for the production of secretory vacuoles in tumoral cells of a live organism, especially for the regression of cancer tumors in mammals.

The medicament according to the invention may advantageously be administered by injection; in such a case, it may be used at doses ranging from 8.5 ng/g of live organism treated to 1.7 µg/g of live organism treated; for the treatment of a tumor, the injection is preferably performed close to the tumor to be treated.

The surprising nature of the invention arises especially from the fact that compounds having a formula similar to those defined by formula (I) have been described previously only mentioning activities that are entirely different than those found for the compounds of formula (I) according to the invention. In French patent 2 047 880, it is indicated that the compounds described have hypocholesterolemiant activity. In the document "Synthetic Communications (1997), 27(11), 1951-1962", it is indicated that the compounds described have antibiotic activity. In the document "Arzneimittel-Forschung (1995), 45 (2), 190-4" and in the document "Anticancer Research (1999), 19 (2A), 1229-1234", it is indicated that the compounds described have cytotoxic activity. As a result, a person skilled in the art could not in any way have foreseen, from this prior art, that the compounds of formula (I) could induce dendritogenesis, neuritogenesis and/or the production of secretory vacuoles in various tumoral cell lines.

The induction of vacuole production was observed in various tumoral cell lines and especially in A549, U937, MCF-7, HT29, PC12 and B16 cells. Dendritogenesis and neuritogenesis were observed on U937 and P19 tumoral cells and also on B16 and PC12 cells.

Several examples of the preparation of the compounds according to the invention will be given hereinbelow. The details relating to the common process used for the preparation of the various compounds given as examples will first be provided: this process is performed in two steps, the first consisting in obtaining an epoxy-sterol and the second consisting in converting said epoxy-sterol into an amino sterol. Examples 1 and 2 each describe the first step for obtaining two different series of 5,6-α-epoxy-sterols. Example 3 describes the second step using the intermediate products of examples 1 and 2, to react them with an amine; examples 4 to 27 describe the products obtained according to example 3 with various amines. Examples 28 and 29 each describe the first step for obtaining two other different series of 5,6-α-epoxy sterols; examples 30 to 47 describe the second step using the intermediate products of example 28 or 29, to react them with an amine.

EXAMPLE 1

Preparation of 5,6-α-epoxycholestan-3β-ol meta-Chloroperoxybenzoic acid (0.73 g, 4.25 mmol, purity of 70-75% by weight) is dissolved in methylene chloride (10 ml) and added dropwise to a mixture of cholesterol (1 g, 2.5 mmol) dissolved in methylene chloride (25 ml). Stirring is continued overnight. The reaction mixture is washed with aqueous sodium sulfite solution (10% by weight) and sodium hydrogen carbonate (5% by weight) and a saturated solution of a mixture of sodium chloride and potassium chloride. The organic phase is dried over anhydrous magnesium sulfate. Evaporation of the organic solvent under vacuum gives 0.7 g of white needles (69.5% yield). The proportion of the α and β isomers of the epoxide was determined by proton NMR at 200 MHz: 78% α epoxide and 22% β epoxide are found (proton 1H NMR: δ 2.89 (d, 1H, J=4.37 Hz, H-6); 3.04 (d, J=2.43 Hz, H-6); 3.91 (m, 1H, H-3);

MS DCI/NH$_3$ MH$^+$ 403. The α and β isomers were separated by liquid chromatography on silica (85/15 toluene/ethyl ether). The α isomer has a melting point m.p.=141-142° C.; the β isomer has a melting point m.p.=131-132° C. To complete the characterization, thin-layer chromatography was performed (ethyl acetate); the following was obtained: Rf=0.69 (brown color after developing with a sulfuric acid/methanol mixture).

EXAMPLE 2

Preparation of 5,6-α-epoxycholest-7-en-3β-ol

7-Dehydrocholesterol (Acros, 1 g, 2.6 mmol) and sodium carbonate (0.55 g, 5.2 mmol) are dissolved in a mixture of methylene chloride (25 ml) and water (25 ml). meta-Chloroperoxybenzoic acid (0.73 g, 4.25 mmol, purity 70-75% by weight) is dissolved in methylene chloride (10 ml) and added dropwise to the mixture maintained under vigorous stirring. After stirring for 10 minutes, the phase is recovered and then washed with an aqueous solution consisting of aqueous sodium sulfite solution (10% by weight), aqueous sodium carbonate solution (5% by weight) and a saturated solution of a mixture of sodium chloride and potassium chloride. The organic phase is dried over anhydrous magnesium sulfate. Evaporation of the solvent and recrystallization of the product from acetone gives 0.7 g of white needles (yield 70%). The structure was confirmed by proton NMR: δ 0.52 (s, 3H, H-19); 2.986 (d, 1H, J=4.1 Hz, H-6); 3.91 (m, 1H, H-3); MS DCI/NH$_3$ MH$^+$ 401. The melting point was determined: m.p.=144-146° C.

EXAMPLE 3

Synthesis of the Amino Sterols from the Epoxy-Sterols

Lithium perchlorate (0.75 mmol) and an amine in its basic form (1 mmol) are dissolved in anhydrous ethanol (1 ml) and added under a flow of argon to an ethanolic solution (3 ml) of an epoxy-sterol obtained according to either of examples 1 and 2 (100 mg, 0.25 mmol). The reaction mixture is kept stirring at reflux, for 6 days in the case of example 1 and for 3 days in the absence of light and at room temperature in the case of example 2. The reaction progress is monitored by thin-layer chromatography (TLC) under conditions adapted to the various amines. The solvent is removed by evaporation and the residue is washed with ethyl ether (5×3 ml) and hexane (5×20 ml). The residue is dissolved in water and acidified with 2M HCl (2 ml). The solution is prepurified on a grafted-silica cartridge (sep-pak cartridge RP C18, 500 mg, Waters) and the excess polyamine is removed by passing water through the cartridge (5 ml). The product is eluted with a 1/1 CH$_2$CN/H$_2$O mixture (5 ml). The product is purified by reverse-phase HPLC by means of a linear gradient of a starting mixture of H$_2$O 95/CH$_3$CN 5/TFA 0.1% up to a mixture of CH$_3$CN 95/H$_2$O 5/TFA 0.1 reached in 60 minutes (flow rate=1 ml/min; λ=210 nm). The fraction of interest was repurified under isocratic conditions using a mobile phase composed of a mixture (CH$_3$CN 95/H$_2$O 5/TFA 0.1) 44%/(H$_2$O 95/CH$_3$CN 5/TFA 0.1%) 56% (flow rate=1 ml/min; λ=210 nm).

EXAMPLE 4

Preparation of cholestane-3β,5α-diol-6β-N-[1-N1-(3-aminopropyl)butane-1,4-diamine]

In example 3, N1-(3-aminopropyl)butane-1,4-diamine is used as amine.

The product obtained is characterized specifically by thin-layer chromatography (TLC) (6/3/1 isopropyl alcohol/28% aqueous ammonia/H$_2$O): Rf=0.62.

Mass spectroscopy was also performed (electrospray): MH$^+$: 548.

EXAMPLE 5

Preparation of cholestane-3β,5α-diol-6β-N-[N,N'-bis(3-aminopropyl)butane-1,4-diamine]

In example 3, N,N'-bis(3-aminopropyl)butane-1,4-diamine is used as amine.

The product obtained is characterized specifically by TLC (6/3/1 isopropyl alcohol/28% aqueous ammonia/H$_2$O): Rf=0.37.

Mass spectroscopy was also performed (electrospray): MH$^+$: 605.5.

EXAMPLE 6

Preparation of cholest-7-ene-3β,5α-diol-6β-N-[1-N-1-(3-aminopropyl)butane-1,4-diamine]

In example 3, N1-(3-aminopropyl)butane-1,4-diamine is used as amine.

The product obtained is characterized specifically by TLC (6/3/1 isopropyl alcohol/28% aqueous ammonia/H$_2$O): Rf=0.62.

Mass spectroscopy was also performed (electrospray): MH$^+$: 546.

EXAMPLE 7

Preparation of cholest-7-ene-3β,5α-diol-6β-N-[N,N'-bis(3-aminopropyl)butane-1,4-diamine]

In example 3, N,N'-bis(3-aminopropyl)butane-1,4-diamine is used as amine.

The product obtained is characterized specifically by TLC (6/3/1 isopropyl alcohol/28% aqueous ammonia/H$_2$O): Rf=0.37.

Mass spectroscopy was also performed (electrospray): MH$^+$: 603.5.

EXAMPLE 8

Preparation of cholest-7-ene-3β,5α-diol-6β-N-[2-ethylamino(1H-imidazol-4-yl)]

In example 3, 2-(1H-imidazol-4-yl)ethylamine is used as amine.

The product obtained is characterized specifically by TLC (MeOH): Rf=0.38.

Mass spectroscopy was also performed (electrospray): MH$^+$: 512.5; m/z: 365.3.

EXAMPLE 9

Preparation of cholestane-3β,5α-diol-6β-N-[2-ethylamino(1H-imidazol-4-yl)]

In example 3, 2-(1H-imidazol-4-yl)ethylamine is used as amine.

The product obtained is characterized specifically by TLC (MeOH): Rf=0.38.

High performance chromatography (HPLC) was also performed using a Perkin-Elmer 200 machine equipped with an "Ultrasep ES100RP18" column (6 μm particles), 250 mm long and 8 mm in diameter, manufactured by the company "Bishoff".

HPLC profile: 44% B λ=220 nm rt=44-50 min

Finally, mass spectroscopy was performed (electrospray): m/z: 514.5 (MH$^+$).

EXAMPLE 10

Preparation of cholest-7-ene-3β,5α-diol-6β-N-(4-aminobutylamine)

In example 3, 4-aminobutylamine is used as amine.

The product obtained is characterized specifically by TLC (8/2 MeOH/28% aqueous ammonia): Rf=0.55.

Mass spectroscopy was also performed (electrospray): m/z: 489 (MH$^+$).

EXAMPLE 11

Preparation of cholest-7-ene-3β,5α-diol-6β-N-{2-[2-(2-aminoethoxy)ethoxy]ethylamine}

In example 3, 2-{2-[2-(2-aminoethoxy)ethoxy]ethoxy}-ethylamine is used as amine.

The product obtained is characterized specifically by TLC (8/2 MeOH/28% aqueous ammonia): Rf=0.8.

Mass spectroscopy was also performed (electrospray): m/z: 549 (MH$^+$).

EXAMPLE 12

Preparation of cholestane-3β,5α-diol-6β-N-[4-(2-aminoethyl)imidazol-1-yl]

In example 3, 2-(3H-imidazol-4-yl)ethylamine is used as amine.

The product obtained is characterized specifically by TLC (8/2 MeOH/28% aqueous ammonia): Rf=0.72.

HPLC was also performed using a Perkin-Elmer 200 machine equipped with an "Ultrasep ES100RP18" column (6 μm particles), 250 mm long and 8 mm in diameter, manufactured by the company "Bishoff".

HPLC profile: 44% B λ 220 nm rt=44-50 min

Finally, mass spectroscopy was performed (electrospray): m/z: 514.5 (MH$^+$).

EXAMPLE 13

Preparation of cholestane-3β,5α-diol-6β-N-({1H-imidazol-4-yl}ethyl)acetamide

In example 3, N-[2-(1H-imidazol-4-yl)ethyl]acetamide is used as amine.

The product obtained is characterized specifically by TLC (1/1 MeOH/ethyl acetate): Rf=0.5.

HPLC was also performed using a Perkin-Elmer 200 machine equipped with an "Ultrasep ES100RP18" column (6 μm particles), 250 mm long and 8 mm in diameter, manufactured by the company "Bishoff".

HPLC profile: 44% Bλ=220 nm rt=44-50 min

Finally, mass spectroscopy was performed (electrospray): m/z: 557 (MH$^+$).

EXAMPLE 14

Preparation of cholestane-3β,5α-diol-6β-(3-aminopropylamine)

In example 3, 1,3-diaminopropane is used as amine.

The product obtained is characterized specifically by TLC (8/2 MeOH/28% aqueous ammonia): Rf=0.50.

Mass spectroscopy was also performed (electrospray) m/z: 447 (MH$^+$).

EXAMPLE 15

Preparation of cholestane-3β,5α-diol-6β-(3-aminopropylacetamide)

In example 3, N-(3-aminopropyl)acetamine is used as amine.

EXAMPLE 16

Preparation of cholestane-3β,5α-diol-6β-(4-aminobutylamine)

In example 3, 1,4-diaminobutane is used as amine.
The product obtained is characterized specifically by TLC (8/2 MeOH/28% aqueous ammonia): Rf=0.51.
Mass spectroscopy was also performed (electrospray) m/z: 491 (MH$^+$).

EXAMPLE 17

Preparation of cholestane-3β,5α-diol-6β-(4-aminobutylyl-1-acetamide)

In example 3, N-(4-aminobutyl)acetamide is used as amine.
The product obtained is characterized specifically by TLC (8/2 MeOH/ethyl acetate): Rf=0.56.
Mass spectroscopy was also performed (electrospray) m/z: 533 (MH$^+$).

EXAMPLE 18

Preparation of cholestane-3β,5α-diol-6β-(6-aminohexylamine)

In example 3, 1,6-diaminohexane is used as amine.
The product obtained is characterized specifically by TLC (8/2 MeOH/28% aqueous ammonia): Rf=0.52.
Mass spectroscopy was also performed (electrospray) m/z: 519 (MH$^+$).

EXAMPLE 19

Preparation of cholestane-3β,5α-diol-6β-(6-aminohexylacetamide)

In example 3, N-(6-aminohexyl)acetamide is used as amine.
The product obtained is characterized specifically by TLC (8/2 MeOH/ethyl acetate: 28%): Rf=0.57.
Mass spectroscopy was also performed (electrospray) m/z: 561 (MH$^+$).

EXAMPLE 20

Preparation of cholestene-7-3β,5α-diol-6β-(3-aminopropylamine)

In example 3, 1,3-diaminopropane is used as amine.
The product obtained is characterized specifically by TLC (8/2 MeOH/28% aqueous ammonia): Rf=0.50.
Mass spectroscopy was also performed (electrospray) m/z: 475 (MH$^+$).

EXAMPLE 21

Preparation of cholestene-7-3β,5α-diol-6β-(3-aminopropylacetamide)

In example 3, N-(3-aminopropyl)acetamide is used as amine.
The product obtained is characterized specifically by TLC (8/2 MeOH/ethyl acetate): Rf=0.54.
Mass spectroscopy was also performed (electrospray) m/z: 517 (MH$^+$).

EXAMPLE 22

Preparation of cholest-7-ene-3β,5α-diol-6β-(4-aminobutylyl-1-acetamide)

In example 3, N-(4-aminobutylacetamide is used as amine.
The product obtained is characterized specifically by TLC (8/2 MeOH/ethyl acetate): Rf=0.56.
Mass spectroscopy was also performed (electrospray) m/z: 531 (MH$^+$).

EXAMPLE 23

Preparation of cholestene-7-3β,5α-diol-6β-(6-aminohexylamine)

In example 3, 1,6-diaminohexane is used as amine.
The product obtained is characterized specifically by TLC (8/2 MeOH/28% aqueous ammonia): Rf=0.51.
Mass spectroscopy was also performed (electrospray) m/z: 517 (MH$^+$).

EXAMPLE 24

Preparation of cholestene-7-3β,5α-diol-6β-(6-aminohexylacetamide)

In example 3, N-(6-aminohexyl)acetamide is used as amine.
The product obtained is characterized specifically by TLC (8/2 MeOH/ethyl acetate): Rf=0.57.
Mass spectroscopy was also performed (electrospray) m/z: 559 (MH$^+$).

EXAMPLE 25

Preparation of cholestane-3β,5α-diol-6β-{[2-(1H-imidazol-4-yl)ethyl]methylamine}

In example 3, [2-(1H-imidazol-4-yl)ethyl]methylamine is used as amine.
The product obtained is characterized specifically by TLC (8/2 MeOH/28% aqueous ammonia): Rf=0.51.
Mass spectroscopy was also performed (electrospray) m/z: 528 (MH$^+$).

EXAMPLE 26

Preparation of cholest-7-ene-3β,5α-diol-6β-{[2-(1H-imidazol-4-yl)ethyl]methylamine}

In example 3, [2-(1H-imidazol-4-yl)ethyl]methylamine is used as amine.
The product obtained is characterized specifically by TLC (8/2 MeOH/28% aqueous ammonia): Rf=0.51.
Mass spectroscopy was also performed (electrospray) m/z: 526 (MH$^+$).

EXAMPLE 27

Preparation of cholest-7-ene-3β,5α-diol-6β-{[2-(1H-imidazol-4-yl)ethyl]methylamine}

In example 3, [2-(1H-imidazol-4-yl)ethyl]methylamine is used as amine.

The product obtained is characterized specifically by TLC (8/2 MeOH/28% aqueous ammonia): Rf=0.51.
Mass spectroscopy was also performed (electrospray) m/z: 526 (MH$^+$).

EXAMPLE 28

Preparation of 5,6-α-epoxy-β-sitostan-3β-ol

In example 1, β-sitosterol is used as sterol.
The product obtained is characterized specifically by TLC (ethyl acetate): Rf=0.69.
Elemental analysis: theory: C=80.87; H=11.70; O=7.43 found: C=80.88; H=11.69; O=7.42.
Mass spectroscopy: DCI/NH$_3$ MH$^+$ 432.

EXAMPLE 29

Preparation of 5,6-α-epoxycampestan-3β-ol

In example 1, campesterol is used as sterol.
The product obtained is characterized specifically by TLC (ethyl acetate): Rf=0.69.
Elemental analysis: theory: C=80.71; H=11.61; O=7.68 found: C=80.66; H=11.63; O=7.72.
Mass spectroscopy: DCI/NH$_3$ MH$^+$ 418.

EXAMPLE 30

Preparation of sitostane-3β,5α-diol-6β-(3-aminopropylamine)

In example 3, 1,3-diaminopropane is used as amine and the epoxide of example 28 is used as epoxide.
The product obtained is characterized specifically by TLC (8/2 MeOH/28% aqueous ammonia): Rf=0.50.
Mass spectroscopy was also performed (electrospray) m/z: 505 (MH$^+$).

EXAMPLE 31

Preparation of sitostane-3β,5α-diol-6β-(3-aminopropylacetamide)

In example 3, N-(3-aminopropyl)-acetamide is used as amine and the epoxide of example 28 is used as epoxide.
The product obtained is characterized specifically by TLC (8/2 MeOH/ethyl acetate): Rf=0.54.
Mass spectroscopy was also performed (electrospray) m/z: 547 (MH$^+$).

EXAMPLE 32

Preparation of sitostane-3β,5α-diol-6β-(4-aminobutylamine)

In example 3, 1,4-diaminobutane is used as amine and the epoxide of example 28 is used as epoxide.
The product obtained is characterized specifically by TLC (8/2 MeOH/28% aqueous ammonia): Rf=0.51.
Mass spectroscopy was also performed (electrospray) m/z: 519 (MH$^+$).

EXAMPLE 33

Preparation of cholestane-3β,5α-diol-6β-(4-aminobutyl-1-acetamide)

In example 3, N-(4-aminobutyl)acetamide is used as amine and the epoxide of example 29 is used as epoxide.
The product obtained is characterized specifically by TLC (8/2 MeOH/ethyl acetate): Rf=0.56.
Mass spectroscopy was also performed (electrospray) m/z: 561 (MH$^+$).

EXAMPLE 34

Preparation of campestane-3β,5α-diol-6β-(3-aminopropylamine)

In example 3, 1,3-diaminopropane is used as amine and the epoxide of example 29 is used as epoxide.
The product obtained is characterized specifically by TLC (8/2 MeOH/28% aqueous ammonia): Rf=0.50.
Mass spectroscopy was also performed (electrospray) m/z: 491 (MH$^+$).

EXAMPLE 35

Preparation of campestane-3β,5α-diol-6β-(3-aminopropylacetamide)

In example 3, N-(3-aminopropyl)acetamide is used as amine and the epoxide of example 29 is used as epoxide.
The product obtained is characterized specifically by TLC (8/2 MeOH/ethyl acetate): Rf=0.54.
Mass spectroscopy was also performed (electrospray) m/z: 533 (MH$^+$).

EXAMPLE 36

Preparation of campestane-3β,5α-diol-6β-(4-aminobutylamine)

In example 3, 1,4-diaminobutane is used as amine and the epoxide of example 29 is used as epoxide.
The product obtained is characterized specifically by TLC (8/2 MeOH/28% aqueous ammonia): Rf=0.51.
Mass spectroscopy was also performed (electrospray) m/z: 505 (MH$^+$).

EXAMPLE 37

Preparation of campestane-3β,5α-diol-6β-(4-aminobutyl-1-acetamide)

In example 3, N-(4-aminobutyl)acetamide is used as amine and the epoxide of example 29 is used as epoxide.
The product obtained is characterized specifically by TLC (8/2 MeOH/ethyl acetate): Rf=0.56.
Mass spectroscopy was also performed (electrospray) m/z: 547 (MH$^+$).

EXAMPLE 38

Preparation of sitostane-3β,5α-diol-6β-(6-aminohexylamine)

In example 3, 1,6-diaminohexane is used as amine and the epoxide of example 28 is used as epoxide.
The product obtained is characterized specifically by TLC (8/2 MeOH/28% aqueous ammonia): Rf=0.53.

EXAMPLE 39

Preparation of sitostane-3β,5α-diol-6β-(6-amino-hexylacetamide)

In example 3, N-(6-aminohexyl)acetamide is used as amine and the epoxide of example 28 is used as epoxide.

The product obtained is characterized specifically by TLC (8/2 MeOH/ethyl acetate): Rf=0.58.

Mass spectroscopy was also performed (electrospray) m/z: 589 (MH$^+$).

EXAMPLE 40

Preparation of campestane-3β,5α-diol-6β-(6-amino-hexylamine)

In example 3, 1,6-diaminohexane is used as amine and the epoxide of example 29 is used as epoxide.

The product obtained is characterized specifically by TLC (8/2 MeOH/28% aqueous ammonia): Rf=0.52.

Mass spectroscopy was also performed (electrospray) m/z: 505 (MH$^+$).

EXAMPLE 41

Preparation of campestane-3β,5α-diol-6β-(6-amino-hexylacetamide)

In example 3, N-(6-aminohexyl)acetamide is used as amine and the epoxide of example 29 is used as epoxide.

The product obtained is characterized specifically by TLC (8/2 MeOH/ethyl acetate): Rf=0.57.

Mass spectroscopy was also performed (electrospray) m/z: 547 (MH$^+$).

EXAMPLE 42

Preparation of sitostane-3β,5α-diol-6β-N-[N,N'-bis(aminopropyl)butane-1,4-diamine]

In example 3, N,N'-bis(3-aminopropyl)butane-1,4-diamine is used as amine and the epoxide of example 28 is used as epoxide.

The product obtained is characterized specifically by TLC (6/3/1 isopropyl alcohol/28% aqueous ammonia/H$_2$O): Rf=0.39.

Mass spectroscopy was also performed (electrospray) m/z: 633.5 (MH$^+$).

EXAMPLE 43

Preparation of campestane-3β,5α-diol-6β-N-[N,N'-bis(aminopropyl)butane-1,4-diamine]

In example 3, N,N'-bis(3-aminopropyl)butane-1,4-diamine is used as amine and the epoxide of example 29 is used as epoxide.

The product obtained is characterized specifically by TLC (6/3/1 isopropyl alcohol/28% aqueous ammonia/H$_2$O): Rf=0.38.

Mass spectroscopy was also performed (electrospray) m/z: 619.5 (MH$^+$).

Mass spectroscopy was also performed (electrospray) m/z: 547 (MH$^+$).

EXAMPLE 44

Preparation of sitostane-3β,5α-diol-6β-N-[1-N1-(3-aminopropyl)butane-1,4-diamine]

In example 3, N1-(3-aminopropyl)butane-1,4-diamine is used as amine and the epoxide of example 28 is used as epoxide.

The product obtained is characterized specifically by TLC (6/3/1 isopropyl alcohol/28% aqueous ammonia/H$_2$O): Rf=0.62.

Mass spectroscopy was also performed (electrospray) m/z: 576 (MH$^+$).

EXAMPLE 45

Preparation of campestane-3β,5α-diol-6β-N-[1-N-1-(3-aminopropyl)butane-1,4-diamine]

In example 3, N1-(3-aminopropyl)butane-1,4-diamine is used as amine and the epoxide of example 29 is used as epoxide.

The product obtained is characterized specifically by TLC (6/3/1 isopropyl alcohol/28% aqueous ammonia/H$_2$O): Rf=0.62.

Mass spectroscopy was also performed (electrospray) m/z: 562 (MH$^+$).

EXAMPLE 46

Preparation of sitostane-3β,5α-diol-6β-N-{[2-(1H-imidazol-4-yl)ethyl]ethylamine}

In example 3, [2-1H-imidazol-4-yl)ethyl]ethylamine is used as amine and the epoxide of example 28 is used as epoxide.

The product obtained is characterized specifically by TLC (MeOH): Rf=0.39.

Mass spectroscopy was also performed (electrospray) m/z: 542.5 (MH$^+$).

EXAMPLE 47

Preparation of campestane-3β,5α-diol-6β-N-{[2-(1H-imidazol-4-yl)ethyl]ethylamine}

In example 3, [2-(1H-imidazol-4-yl)ethyl]ethylamine is used as amine and the epoxide of example 29 is used as epoxide.

The product obtained is characterized specifically by TLC (MeOH): Rf=0.39.

Mass spectroscopy was also performed (electrospray) m/z: 528.5 (MH$^+$).

Examples 48 et seq relate to the use of the compounds according to the invention.

EXAMPLE 48

Dendritogeneses

1) On C57BL/6 Mouse Spleen Monocytes 5-week-old mice are sacrificed by cervical dislocation. They are then dissected. The spleens are removed under sterile conditions and then placed in a cold solution (4° C.) containing serum-free culture medium supplemented with antibiotics (streptomycin and penicillin). The spleens are ground in a sterile fume cupboard and then filtered through a 100 µm filter. The eluate is recovered and then centrifuged at 1000 rpm for 5 minutes at 4° C. The cell pellet is resuspended in phosphate-buffered saline (PBS) solution containing collagenase, the purpose of which is to lyze the red blood cells. The suspension is centrifuged at 1000 rpm and the cells are then resuspended in PBS. The washing operation is performed twice. The final resuspension is performed in whole culture medium, and the cells are counted and distributed into six-well dishes at a density of 40 000 cells/ml. Four hours later, the adhering cells are washed vigorously with PBS in order to remove the cells that might remain attached to the adhering cells or to the culture dish.

FIG. 1 shows the major morphological changes on the mouse monocytes obtained as indicated above, the conversion resulting in dendritic cells. The conversion was obtained with a dose of 1 nM, the photograph having been taken 36 hours after the start of action of the product. The test product is that of example 9. The appearance of cellular extensions is observed, which is one of the main characteristics of activated dendritic cells.

At the same time of treatment of the cells, it was observed that IL-4 and GM-CSF were ineffective; it was also observed that the compounds used for the synthesis of the test compound of formula (I), i.e. cholesterol, the epoxy-cholesterol derivative and the amine, were also ineffective.

Similar results were obtained with the compounds of examples 8, 10, 11, 46 and 47.

2) On U-937 Human Myeloid Leukemia Cells

Figure 3:
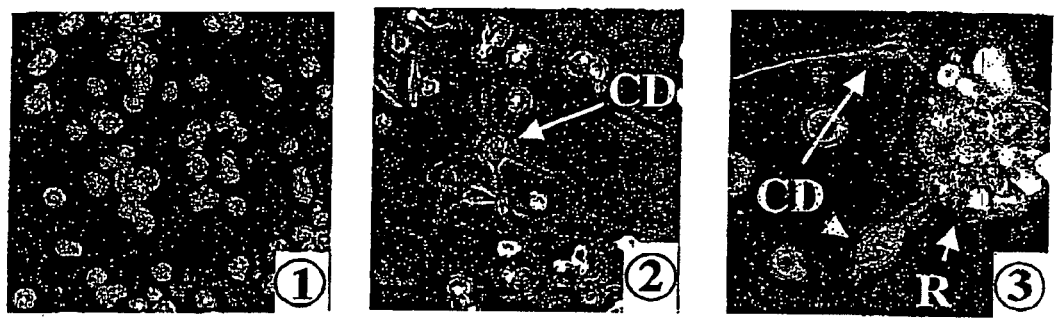
FIG. 3 shows the induction of differentiation of the U-937 cells into dendritic cells by means of the compound cholestane-3β,5α-diol-6β-N-[2-ethylamino(1H-imidazol-4-yl)] of example 9 Photograph 1 shows the cells after treatment with 10 ng/ml of phorbol myristyl acetate (PMA) so as to make them adhere to the bottom of the culture dishes. Photograph 2 makes it possible, after treatment for 2 days with 1 nM of the compound of example 9, to observe the appearance of dendritic cells (CD). Photograph 3 shows, after treatment for 5 days, the increase in the size of the dendrites (up to 100 µm) and the formation of a large number of rosettes (R) consisting of an aggregate of entangled cells.

FIG. 3 shows the induction of differentiation of the U-937 cells into dendritic cells by means of the compound of example 9.

Photograph 1 shows the cells after treatment with 10 ng/ml of phorbol myristyl acetate (PMA) so as to make them adhere to the bottom of the culture dishes. Photograph 2 makes it possible, after treatment for 2 days with 1 nM of the compound of example 9, to observe the appearance of dendritic cells (CD). Photograph 3 shows, after treatment for 5 days, the increase in the size of the dendrites (up to 100 µm) and the formation of a large number of rosettes (R) consisting of an aggregate of entangled cells.

The same observations are made when the compound of example 9 is replaced with the compound of example 46 or 47.

EXAMPLE 49

Neuritogeneses

1) On PC12 Cells

The PC12 cells were cultured at an initial density of 1.5× $10^5$ cells/ml in RPMI 1640 medium supplemented with 10% fetal calf serum and 5% horse serum. The base of the culture dishes is treated with a 0.1 wt % polylysine or collagen solution in order to cause adhesion of the cells. The supernatant cells are removed after 12 hours and then treated with or without nerve growth factor (NGF) at 10 ng/ml, with or without the compound of example 6 or of example 7. The cells are observed by phase-contrast microscopy.

The "control" PC12 cells were treated with the solvent-vehicle used for the test compounds (i.e.: water+0.1 wt % ethanol): these "control" cells appear round and do not change morphologically over time.

The PC12 cells treated by means of the compound of example 6 were treated at a dose of 10 nM, the action time of the compound being 36 hours.

Figure 2:
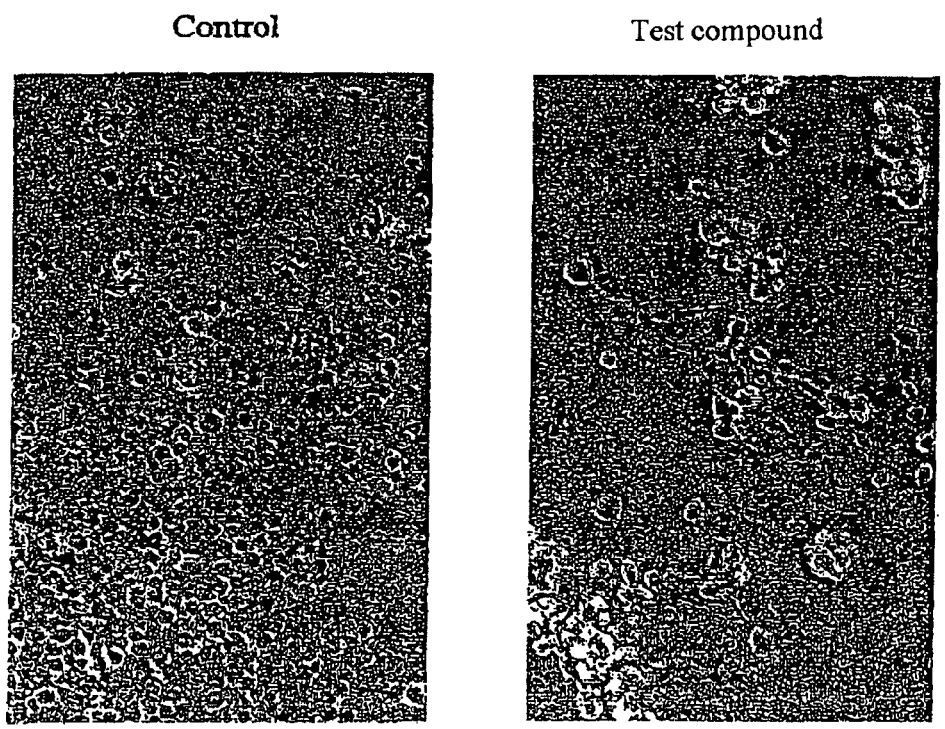
FIG. 2 shows PC12 cells (control) treated with the compound cholest-7-ene-3β5α-diol-6β-N-[1-N1-(3-aminopropyl)butane-1,4-diamine] of Example 6 gradually change toward the formation of dendrites (test compound).

The PC12 cells treated with the compound of example 6 change rapidly in morphology; they become ovoid after treatment for 2 to 4 hours; next, the appearance of excrescences is observed, which change gradually toward the formation of dendrites (see FIG. 2). It is observed that these PC12 cells are bi-polarized.

After 4 hours of treatment of the PC12 cells with the compound of example 6, the appearance of cell adhesion foci is observed in the culture dishes. These foci are 4 to 6 times more numerous than in the case of cells treated with NGF used at doses of 10 ng/ml. The test compound causes the growth of dendrites on the PC12 cells under conditions similar to those indicated previously for the treatment with the compound of example 6. The same observations are made when the compound of example 6 is replaced with the compound of one of the examples 4, 5, 7, 42, 43, 44 and 45.

2) On Mouse P19 Cells

The P19 cells are derived from a mouse embryonic carcinoma. They are pluripotent cells, which can change into neurones or into glial cells by treatment with retinoic acid (J. Cell. Biol. 1982 August, 94 (2): pp. 253-262) and can differentiate into muscle cells in the presence of dimethyl sulfoxide (Nature 1982-9 September, 299(58 79): pp. 165-167).

The P19 cells are cultured in the presence of an "RPMI 1640" culture medium sold by the company "Gibco BRL", this medium being supplemented with 2 mM of glutamine and 4% by weight of fetal calf serum. They are inoculated at low density (10 000 cells per 60-mm well). The P19 cells are treated with the compound of example 6; they are then observed by phase-contrast microscopy. These cells were treated at a dose of 10 nM, the action time of the compound being 36 hours.

Figure 16:
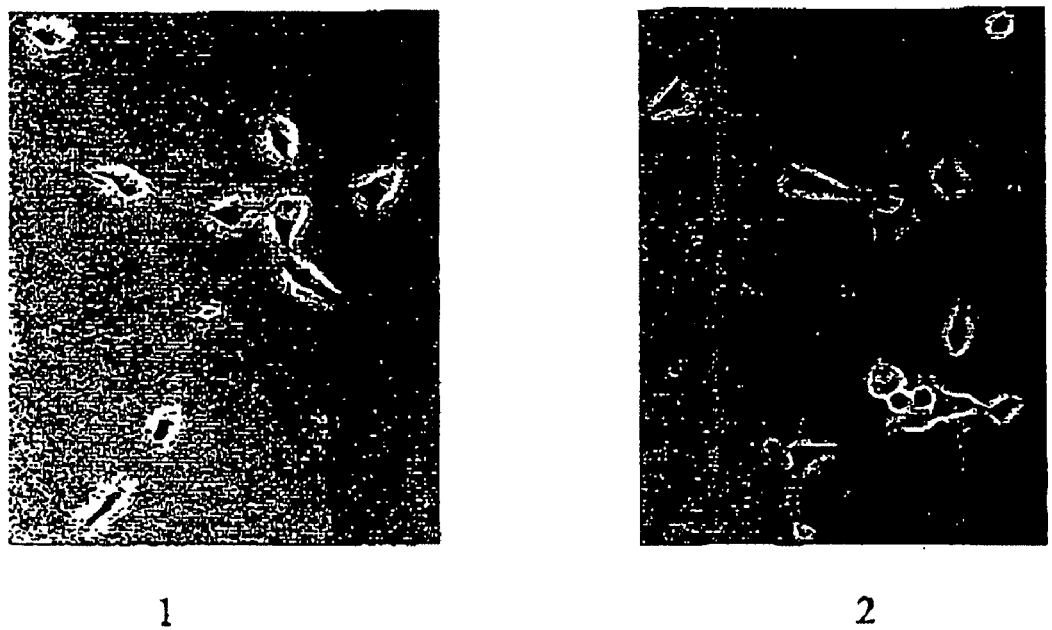
FIG. 16 shows The change in morphology of P19 cells treated with the compound cholest-7-ene-3β,5α-diol-6β-N-[1-N1-(3-aminopropyl)butane-1,4-diamine] of example 6 after 12 hours of treatment: the appearance of cellular extensions is observed, which change toward the formation of dendrites. Photograph 1 corresponds to a blank control and photograph 2 corresponds to the test compounds.

The P19 cells treated with the compound of example 6 change in morphology after 12 hours of treatment: the appearance of cellular extensions is observed, which change toward the formation of dendrites (see FIG. 16, in which photograph 1 corresponds to a blank control and photograph 2 corresponds to the test compounds).

The same observations are made when the compound of example 6 is replaced with the compound of one of the examples 4, 5, 7, 42, 43, 44 and 45.

EXAMPLE 50

Appearance of Surface Antigens Characteristic of the State of Differentiation of the CDs The study was performed on CDs derived from C57BL/6 mouse splenocytes, from human PBMC and from U937 myeloid leukemia cells. The cells derived from C57BL/6 mouse splenocytes were prepared as indicated in example 48.1.

The phenotypes are analyzed by flow cytometry on an "FAC Scan Flow" machine (Beckton Dikinson, BD Bioscience, Franlin Lakes, N.J., USA) using FITC-conjugated antibodies (HLA-DR, CD-80, LAMP-11) and phycoerythrine-conjugated antibodies (anti-CD-83, CD-86 and CD-40, all originating from "BD Bioscience").

For the compound of example 9, the results are given in the table below:

Phenotype of Dendritic Cells Stimulated with the Compound of Example 9

| Phenotype | CDs derived from C57BL/6 mouse monocytes | CDs derived from U-937 cells | CDs derived from human monocytes |
|---|---|---|---|
| Class I CMH | +++ | +++ | +++ |
| Class II CMH | +++ | +++ | +++ |
| CD80 | +++ | +++ | +++ |
| CD40 | +++ | +++ | +++ |
| CD86 | + | + | +++ |
| LAMP-II | + | + | + |
| CD83 | ND | + | + |

ND = not determined

EXAMPLE 51

Production of IL-12p70 and IL-10 by the Dendritic Cells

The culture supernatants are frozen at a temperature of −80° C. until the time of testing for the presence of cytokines. The presence of IL-12p70 and IL-10 is measured using ELISA kits obtained from "Endogen" (Woburn, Mass., USA).

Figure 4:
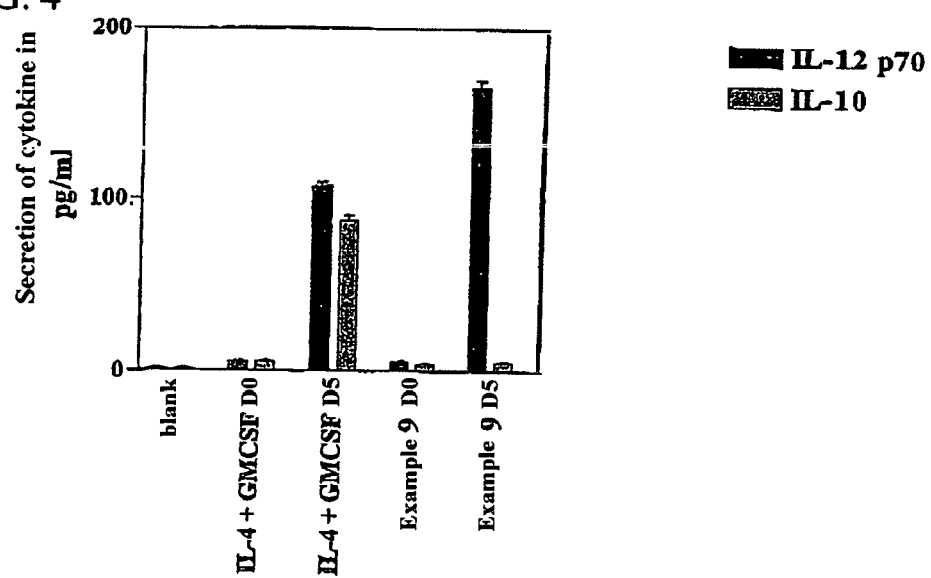
FIG. 4 shows the production of cytokines (p70 subunit of IL-12, and IL-10) by the U-937 cells treated with the compound cholestane-3β,5α-diol-6β-N-[2-ethylamino(1H-imidazol-4-yl)] of Example 9.

FIG. 4 shows the production of cytokines by the U-937 cells treated with the compound of example 9. It is observed that the treatment stimulates the production of the p70 subunit of IL-12 from 36 hours after the start of the treatment. This phenomenon continues for the two weeks of treatment. This same treatment does not stimulate the transcription of IL-10 for treatments extending over a period of two weeks: this result is particularly advantageous since it is known that IL-10 has immunosuppressant properties, which block the differentiation of dendritic cells, and that the couple (IL-4+GM-CSF) stimulates the production of IL-10.

The same observations were made when the compound of example 9 was replaced with the compound of one of the examples 46 and 47.

EXAMPLE 52

Proliferation of T Lymphocytes

C57BL/6 mouse monocytes were collected as indicated in example 48.1. The dendritic cells were obtained as indicated in example 9. After transformation into CDs with the test compound, the cells are treated with an antimitotic agent (mitomycin C at 0.0006 mg/ml) and incubated for 30 minutes at 37° C., in order to block DNA synthesis in the CDs. After this treatment, the cells are washed twice with RPMI 1640 medium supplemented with 10% fetal calf serum.

BALB/c mouse spleens were also collected and treated as described for the preparation of the C57BL/6 mouse monocytes. The nonadherent cells, which contain the T lymphocytes, are recovered and added to the C57BL/6 mouse dendritic cells. On the fourth day of contact of the cells, tritiated thymidine is added. After incubation for 18 hours, the cells are lyzed with absolute alcohol. The precipitate is suspended in water and then filtered through a cellulose filter. The incorporation of thymidine is measured by scintillation counting (Packard Instrument, Meriden Conn., USA).

Figure 5:
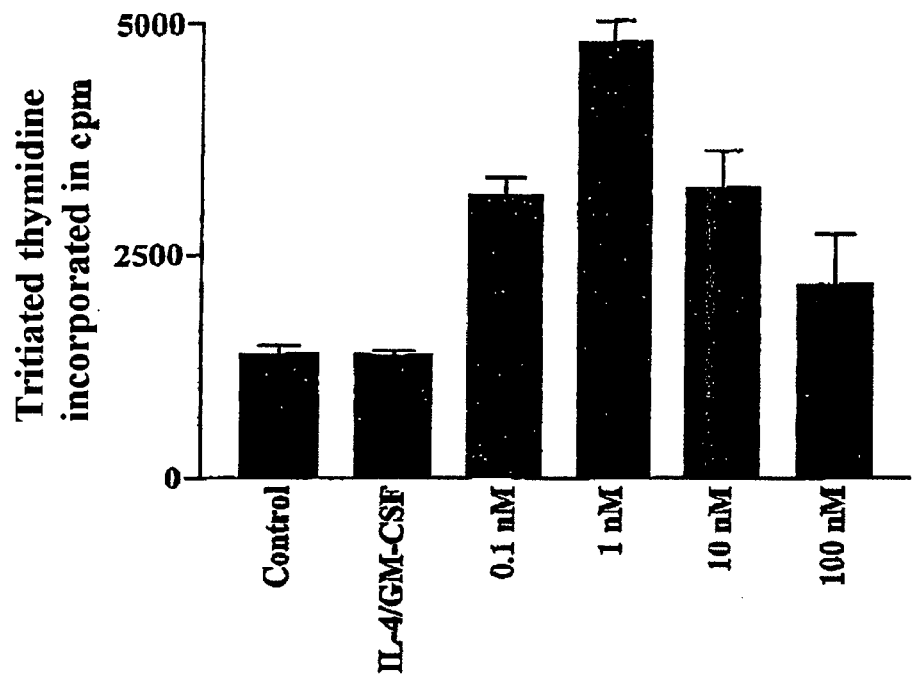
FIG. 5 shows the activation of the T lymphocytes with the dendritic cells produced under the effect of the compound cholestane-3β,5α-diol-6β-N-[2-ethylamino(1H-imidazol-4-yl)] of example 9.

FIG. 5 shows the activation of the T lymphocytes with the dendritic cells produced under the effect of the compound of example 9. The adherent monocytes originating from mouse spleens obtained according to example 14.1 were treated with the abovementioned compound at variable doses. The dendritic cells thus obtained were placed in contact with the T lymphocytes originating from BALB/c mouse spleens. The lymphocyte proliferation is measured by measuring the incorporation of tritiated thymidine into the DNA.

It is found that the test compound induces a stimulation of the T lymphocyte proliferation by a factor of 5. If the same cells are treated with the couple (IL-4/GM-CSF) followed by a treatment with TNFα, the proliferation effect is observed only to a much lower level, since this effect corresponds to a factor of 1.4.

The same observations were made when the compound of example 9 was replaced with the compound of one of the examples 46 and 47.

EXAMPLE 53

Proliferation of Mouse Mammary Adenocarcinoma Cells (TS/A (H-$2^d$)) in Culture

The mouse tumoral line TS/A(H-$2^d$) is a cell line of a spontaneous mammary adenocarcinoma of syngenic mice of BALB/c mice. They are cultured in mycoplasm-free controlled RPMI 1640 medium supplemented with endotoxin-free controlled fetal calf serum (Girco-Brio, 2 mM of glutamine, 100 U/ml of penicillin, 50 μg/ml of streptomycin, essential amino acids and sodium pyruvate.

Figure 6:
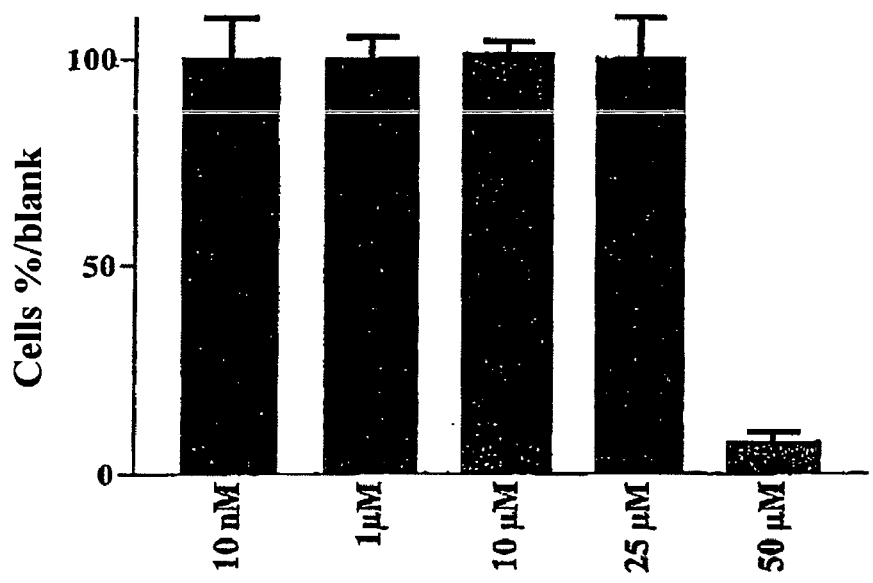
FIG. 6 shows the cytotoxicity on TS/A in vitro: the tumoral cells were treated with variable doses of the compound cholestane-3β,5α-diol-6β-N-[2-ethylamino(1H-imidazol-4-yl)] of example 9.

FIG. 6 shows the cytotoxicity on TS/A in vitro: the tumoral cells were treated with variable doses of the compound of example 9. The cytotoxicity appears for doses of 50 μM. The doses chosen to perform the tests on the tumors implanted onto the BALB/c mice were doses of 5 nM and 1 μM, for which no toxicity is observed, irrespective of the incubation time with the cells.

EXAMPLE 54

Growth Tests on Tumors Implanted onto BALB/c Mice

The tumors are implanted in the following manner: 1×$10^6$ TS/A cells are inoculated by intradermal injection into the right side of the abdomen of 5-6-week-old BALB/c mice (Janvier breeding station, Le Genest Saint Isle).

Figure 7:
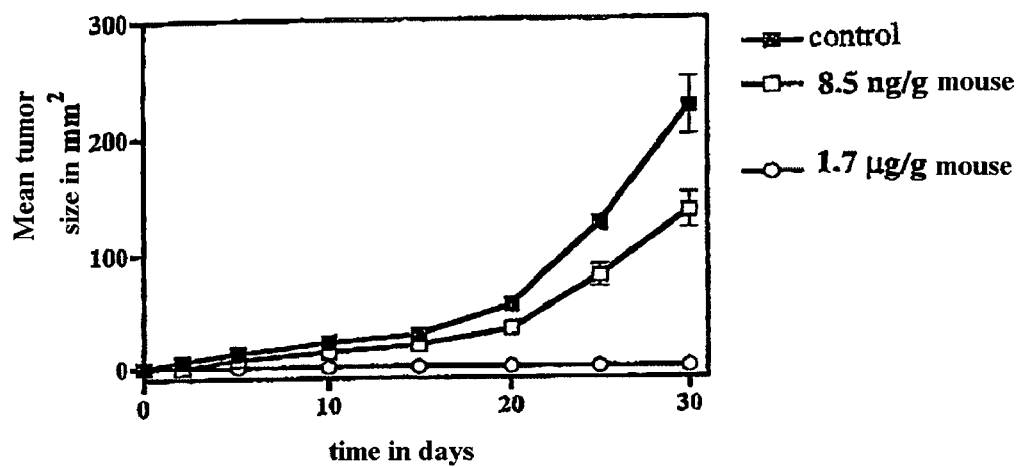
FIG. 7 shows the results of growth tests on tumors, where the test molecule is the compound cholestane-3β,5α-diol-6β-N-[2-ethylamino(1H-imidazol-4-yl)] of example 9, which is injected intradermally on the third day in the region of the tumor.

The test molecule is the one corresponding to example 9; it is injected on the third day intradermally in the region of the tumor; the result is shown in FIG. 7.

In the absence of the compound, the tumors appear within four days and grow over a period of 30 days. Relative to the control mice, a slowing-down effect appears for a dose of test compound of 8.5 ng/g of mouse. At a dose of 1.7 μg/g of mouse, no tumor is detectable on the mice. This illustrates the extreme efficacy of the treatment. The anatomopathology analyses show that no trace of necrosis is observable in the area of injection of the test compound. For the mice treated with the test compound, at a dose of 1.7 μg/g, whether or not a tumor has been implanted, hyperplasia of the peripheral lymphoid system is observed, indicating activation of the immune system.

Figure 17:
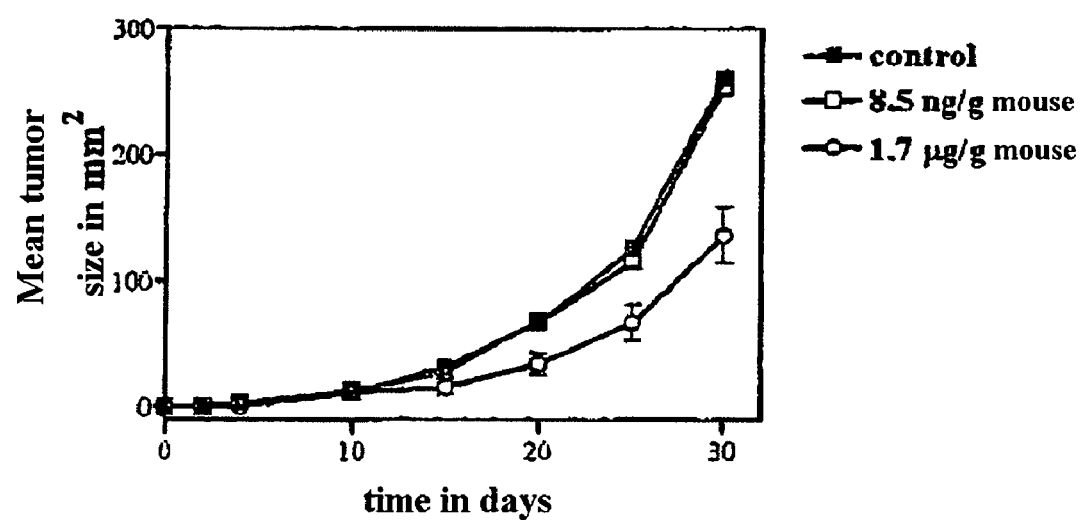
FIG. 17 shows the efficacy of the compound cholestane-3β,5α-diol-6β-N-[2-ethylamino(1H-imidazol-4-yl)] of example 9 for an administration of this test compound remote from a tumor. Injection is performed on the third day after implantation of a tumor, intradermally into the controlateral position relative to said implantation. In this experiment, a slowing-down of the tumoral growth is observed relative to the control mice, for a dose of 1.7 µg/g of mouse.

The same experiment as that described above was repeated, changing the area of injection of the molecule corresponding to example 9; the injection is performed on the third day after implantation of the tumor, intradermally into the controlateral position relative to said implantation. In this experiment, a slowing-down of the tumoral growth is observed relative to the control mice, for a dose of 1.7 µg/g of mouse. This illustrates the efficacy of the treatment for an administration of the test compound remote from the tumor. The results obtained are represented by the curves in FIG. 17.

The same observations were made when the compound of example 9 was replaced with the compound of one of the examples 46 and 47.

EXAMPLE 55

Induction of Vacuole Production in the A549 Tumoral Cell Line

A549 cells were treated with 100 nM of compound according to example 9, for 12 hours.

The A549 cells were obtained from the American Tissue Culture Collection (ATCC); they were inoculated at a density of 50 000 cells per well into 12-well plates and were cultured in RPMI medium supplemented with 5% fetal calf serum. To perform the treatment with the compound according to the invention, the cells are incubated with said compound (or with a control product) for 48 hours. The cells are then observed by phase-contrast microscopy every four hours to monitor the formation of vacuoles, and are then fixed with 0.4% paraformaldehyde solution in phosphate-buffered saline (PBS) at pH 7.4.

Figure 8:
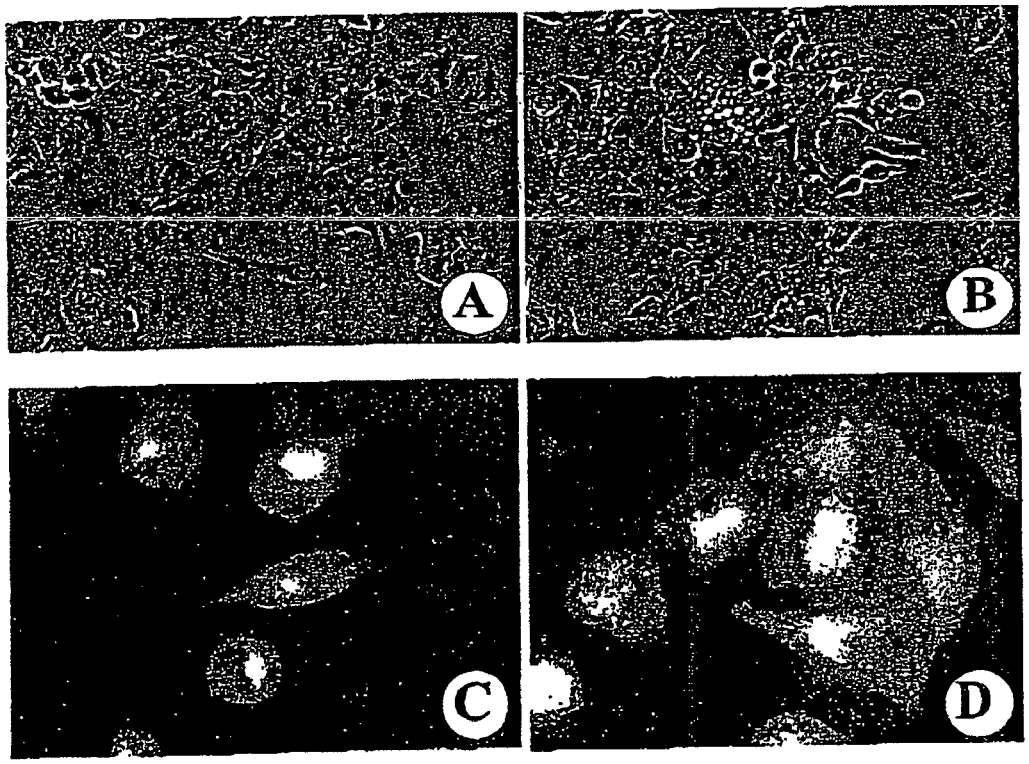
FIG. 8 shows phase-contrast microscopy results of A59 cells treated with the compound cholestane-3β,5α-diol-6β-N-[2-ethylamino(1H-imidazol-4-yl)] of example 9. Photograph A shows the cells before treatment and photograph B after treatment; in photograph C, the cells were treated with the solvent vehicle; and in photograph D, it is observed that the treatment with the compound according to the invention leads to a massive appearance of vacuoles.

The result is shown in FIG. 8 (phase-contrast microscopy). Photograph A shows the cells before treatment and photograph B after treatment; in photograph C, the cells were treated with the solvent vehicle; and in photograph D, it is observed that the treatment with the compound according to the invention leads to a massive appearance of vacuoles.

To obtain photograph D indicated above, the process was performed as follows: after treating the cells, the culture medium is removed and the cells are washed with PBS at pH 7.4. The cells are incubated for 10 minutes with 1 µM solutions of monodansyl cadaverine (MDC). They are then rinsed thoroughly with PBS solution at 4° C. One drop of "Vectashield" solution (Vector Laboratories, CA) is added before mounting between microscope slide and cover slip: the cells are then observed rapidly under the microscope and photographed. Photograph D of FIG. 8 shows numerous fluorescent vacuoles in the cells.

It is thus seen that the test compound induces a massive production of cytoplasmic vacuoles in the A549 human tumoral line. The effect observed is dose-dependent and appears six hours after the treatment. It reaches a maximum 12 hours after the treatment.

The same observations were made when the compound of example 9 was replaced with the compound of one of the examples 46 and 47.

It was found that the compound of example 8 also showed a similar effect. In addition, a similar phenomenon was observed on U-937, PC-12, MCF-7, HELA, COS-7, HEK-293, HEK-293T, NIH-3T3, HT-29 and CHO cells obtained and treated as indicated above for the A549 cells.

When the cell treatment is stopped by replacing the growth medium with fresh medium, the vacuoles disappear: this shows that the effect of the compound according to the invention is reversible.

Figure 11:
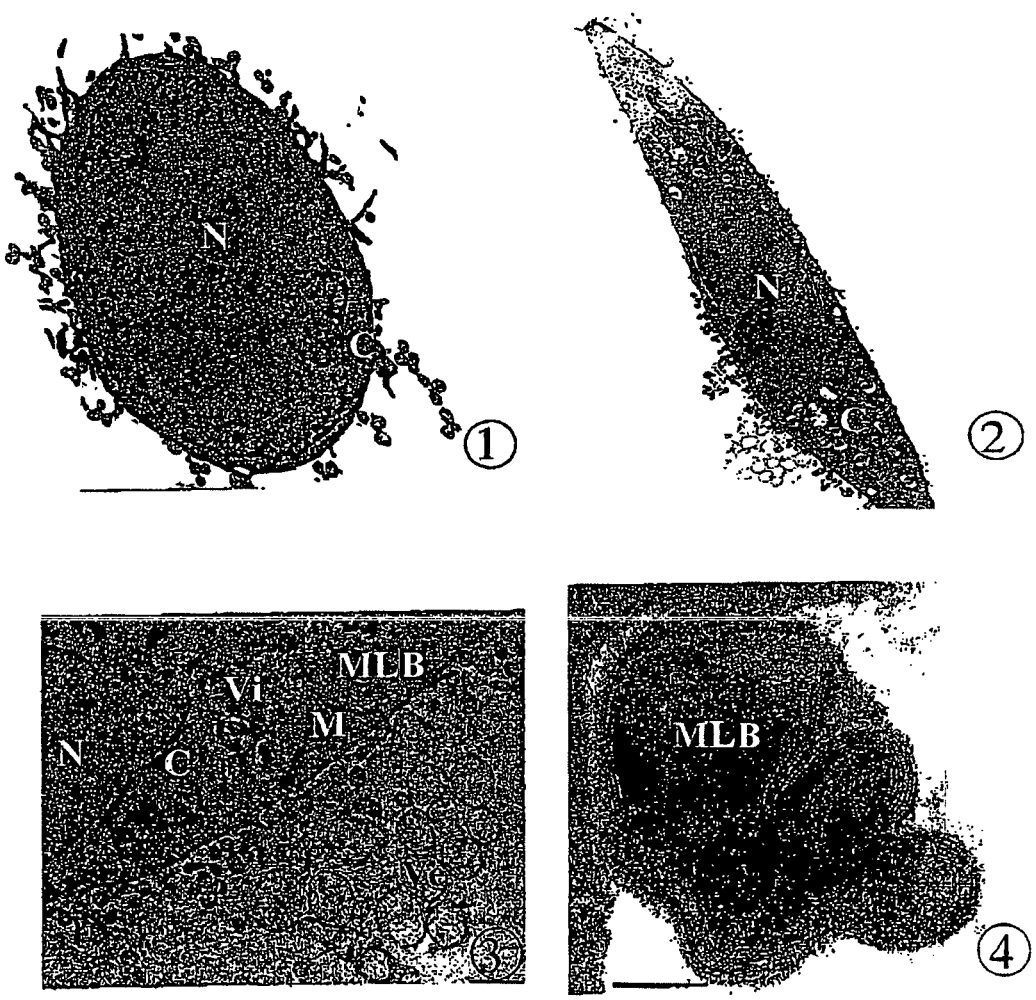
FIG. 11 shows A549 cells treated the compound cholestane-3β,5α-diol-6β-N-[2-ethylamino(1H-imidazol-4-yl)] of example 9 examined by electron microscopy.

The A549 cells treated as indicated above with the compound according to example 9 were also examined by electron microscopy. To examine these A549 cells by electron microscopy, they are fixed using a solution of PBS containing 3% glutaraldehyde, taken up in resin (EPON) and finally cut into thin slices using an ultra-microtome. These slices are then placed on 200-mesh copper grilles and examined by electron microscopy. The results are given in FIG. 11. FIG. 11.1 shows the "control" cells (magnification: 6000); FIG. 11.2 shows the cells treated with the compound of example 9 (magnification: 4000); FIG. 11.3 shows a magnification of the vesicles that can be seen in FIG. 11.2 (magnification: 25 000); FIG. 11.4 shows a detail of the content of an intracytoplasmic vacuole (magnification: 72 000). In this FIG. 11, the letters used have the following meanings: N=nucleus; C=cytoplasm; M=mitochondria; Vi=intracytoplasmic vesicles; Ve=extracellular vesicles; MLB=multilamellar body.

Detailed analysis of the photographs of FIG. 11 allows the following observations: FIG. 11.1 shows a cell with a central voluminous nucleus, surrounded by the cytoplasm; at the surface of the cell are small extensions, which are villi. Photograph 11.2 shows the cell after it has undergone a treatment with the compound according to the invention; it has adopted a spindle-shaped morphology; the villi are concentrated on one face of the cell (in the bottom-right corner in FIG. 11.2), where numerous vacuoles appear at the surface; numerous vacuoles and mitochondria are also observed in the cytoplasm. Photograph 11.3 shows numerous mitochondria and vacuoles, which contain dark bodies and which are surrounded by cytoskeleton fibers; in this view, two types of vacuole can be seen: intracytoplasmic vacuoles (Vi) and extracytoplasmic vacuoles (Ve). FIG. 11.4 shows a detail of a structure contained in the intracytoplasmic vacuoles; it is a multilamellar body characteristic of pulmonary cells producing proteins of surfactant B type.

EXAMPLE 56

Survival of PC12 Cells

PC12 cells were treated as indicated in example 49.1. In the case of the present example, they are treated with increasing doses of a compound according to the invention used at 100 nM; they are kept in culture dishes for three weeks. The number of live cells is measured every two days. The test compound is added every two days for the first six days of the treatment.

Figure 9:
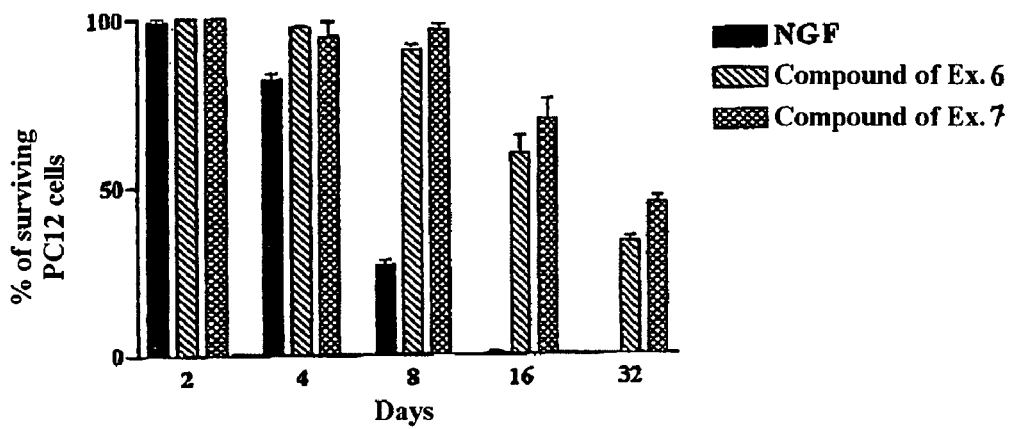
FIG. 9 shows PC12 cells were treated with the compound cholest-7-ene-3β,5α-diol-6β-N-[1-N1-(3-aminopropyl)butane-1,4-diamine] of example 6 and the compound cholest-7-ene-3β,5α-diol-6β-N-[N,N'-bis(3-aminopropyl)butane-1, 4-diamine] of example 7. The PC12 cells were incubated with each of these test compounds and with 10 ng/ml of NGF. The results are expressed as mean percentages of survival of the PC12 cells for three independent experiments.

This test was performed with the compound of example 6 and the compound of example 7. The PC12 cells were incubated at 37° C. with each of the test compounds and with 10 ng/ml of NGF: these substances were added to the culture medium during the inoculation. The results are expressed as mean percentages of survival of the PC12 cells for three independent experiments: they are shown in FIG. 9.

The same observations are made when the compound of example 6 is replaced with the compound of one of the examples 4, 5, 42, 43, 44 and 45.

The PC12 cells thus treated are maintained in culture after having undergone the dendritic growth, the existence of which was established by example 15. It is found that the survival of these cells is, relative to the use of NGF, considerably increased when the compounds according to the invention are used.

EXAMPLE 57

Survival of Motor Neurones

Figure 10:
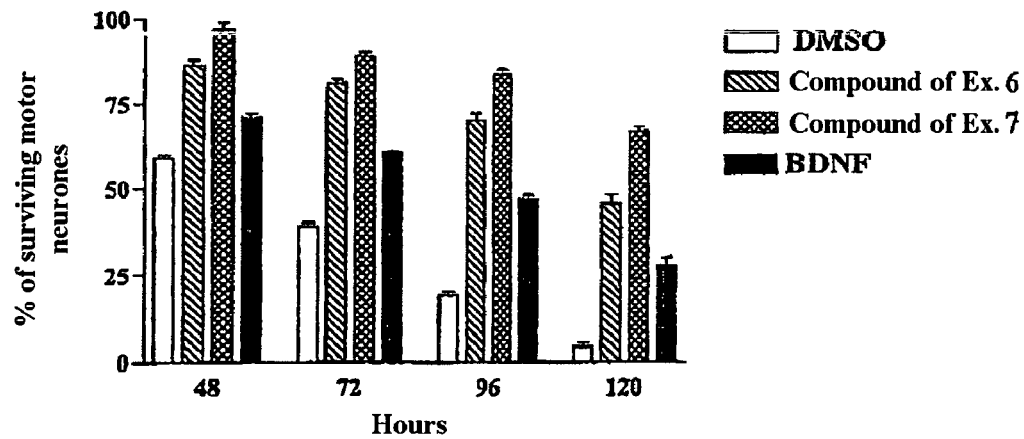
FIG. 10 shows purified motor neurones treated with the compound cholest-7-ene-3β,5α-diol-6β-N-[1-N1-(3-aminopropyl)butane-1,4-diamine] of example 6 and the compound cholest-7-ene-3β,5α-diol-6β-N-[N,N'-bis(3-aminopropyl)butane-1,4-diamine] of example 7. The purified motor neurones were incubated with 10 ng/ml of BDNF or with test compounds at a concentration of 100 nM.

Mouse neurones were extracted and kept in culture according to the method described by Duong et al., British Journal of Pharmacology, 1999, vol. 28, pp. 1385-1392. The cells kept in culture were treated with the solvent-vehicle used (water+ 0.02% dimethyl sulfoxide), with a neurotrophic factor (i.e. BDNF, "Brain Derived Neurotrophic Factor") or with a compound according to the invention. Variable doses of compound were used in order to evaluate the properties of the compounds according to the invention on normal motor neurones. The methodology used for the culturing and counting of the surviving cells is the same as that defined in example 56; the purified motor neurones were incubated at 37° C. with the solvent-vehicle indicated above, with 10 ng/ml of BDNF or with the compound of example 6 or of example 7, at a concentration of 100 nM. The results are shown in FIG. 10.

The same observations are made when the compound of example 6 is replaced with the compound of one of the examples 4, 5, 42, 43, 44 and 45.

It is found that in the absence of treatment with a compound according to the invention or with BDNF, the cells rapidly disappear within a few days. It is found that the efficacy of any of the compounds according to the invention that were tested is superior to that of BDNF: the addition of a compound according to the invention thus results not only in dendritic growth (as established by example 49), but also in survival of the cells for a period of three weeks.

The survival tests given in examples 56 and 57 indicate a favorable effect of the molecules on neurodegenerative diseases such as amyotrophic lateral sclerosis (Amyotroph. Lateral Scler. Other Motor Neuron Discord (2001) 2 March; suppl. 1: S 55-68) or Alzheimer's disease and Parkinson's disease (Brain Research Review (2000) vol. 3, pp. 199-227).

EXAMPLE 58

Actin Skeleton on Treated A549 Cells

A549 cells were treated with the compound of example 9 according to the protocol described in detail in example 55; they are inoculated onto glass slides placed at the bottom of six-well culture dishes (NUNC) at a density of 50 000 cells per well in a nutrient medium of "RPMI 1640" type sold by the company "Gibco BRL", supplemented with 10% fetal calf serum. The cells are then fixed with 3% paraformaldehyde solution and are permeabilized with a detergent solution containing 0.1% "Triton-X-100" in PBS. The actin skeleton of the treated cells was observed by labeling the cells with phalloidin-FITC.

Figure 12:
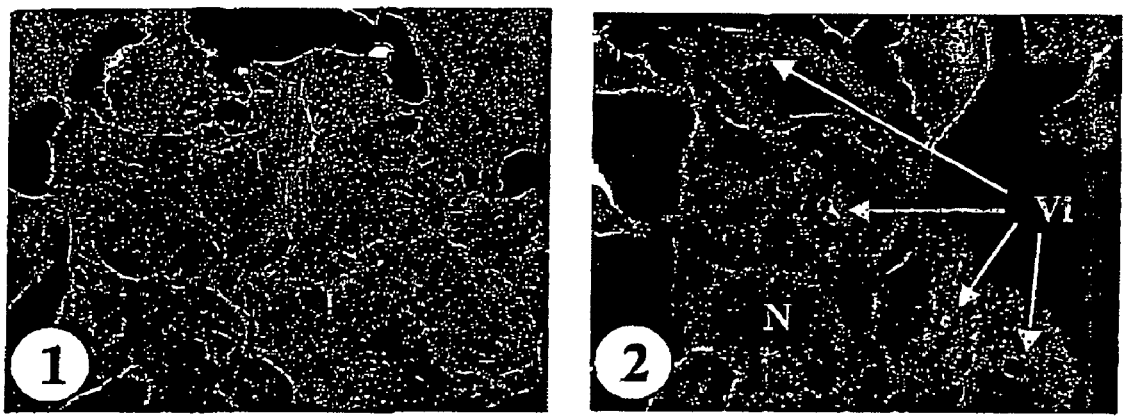
FIG. 12 shows A549 cells were treated with the compound cholestane-3β,5α-diol-6β-N-[2-ethylamino(1H-imidazol-4-yl)] of example 9. The actin skeleton of the treated cells was observed by labeling the cells with phalloidin-FITC. Photograph 1 of FIG. 12 shows the control A549 cells: the actin cytoskeleton holds the cells in a regular manner. Photograph 2 of FIG. 12 shows the appearance of refringent vesicles, which are surrounded by actin.

The result is shown in FIG. 12: photograph 1 of FIG. 12 shows the control A549 cells: the actin cytoskeleton holds the cells in a regular manner. Photograph 2 of FIG. 12 shows the appearance of refringent vesicles, which are surrounded by actin; such vesicles are also apparent on the exterior of the cell: it is thought that actin intervenes as a motor during the secretion of the exocytosis vacuoles demonstrated in example 55.

Figure 13:
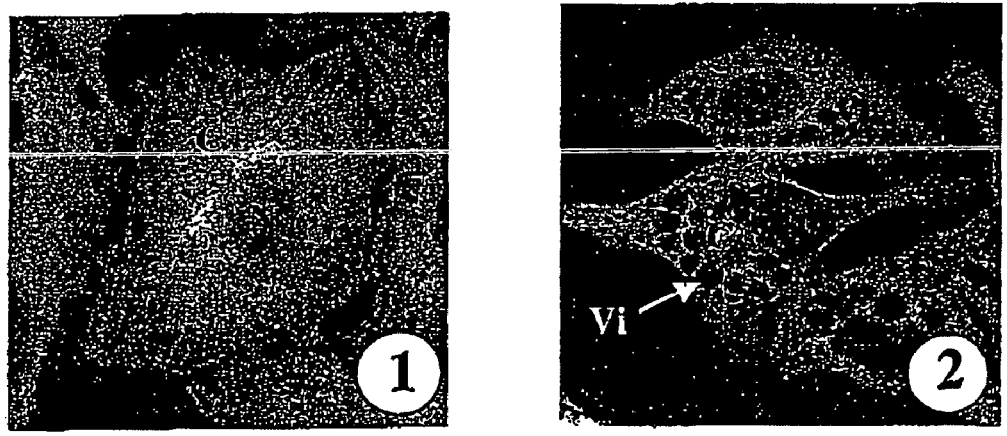
FIG. 13 shows the observation of the tubulin skeleton by fluorescence microscopy of the A549 cells shown for FIG. 12. Photograph 1 shows an untreated control cell and photograph 2 shows a cell treated according to the process given in detail in example 21. In this case, the A549 cells are labeled with an anti-γ-tubulin antibody and developed with an anti-IgG-FITC antibody.

FIG. 13 shows the observation of the tubulin skeleton on the A549 cells by fluorescence microscopy. Photograph 1 shows an untreated control cell and photograph 2 shows a cell treated according to the process given in detail in example 21. In this case, the A549 cells are labeled with an anti-γ-tubulin antibody and developed with an anti-IgG-FITC antibody.

Photograph 1 shows a regular filamentous network. Photograph 2 shows the presence of intracytoplasmic vacuoles, which are not surrounded with γ-tubulin (appearance of numerous holes delimiting the presence of these vacuoles).

The combined observations of FIGS. 12 and 13 show that the cytoskeleton fibers observable by electron microscopy in the treated A549 cells contain actin fibers.

The same observations were made when the compound of example 9 was replaced with the compound of one of the examples 46 and 47.

EXAMPLE 59

Induction of Vacuole Production in the U937 Tumoral Cell Line

U937 cells were treated with 10 nM of the compound according to example 9 for 24 hours. The treatment methods are those described in detail in example 55.

Figure 14:
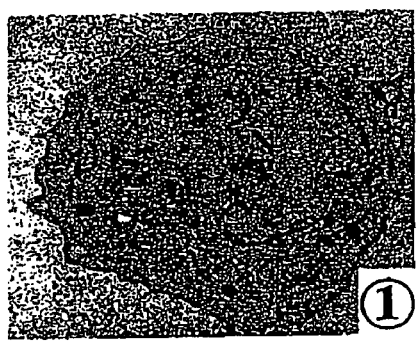
FIG. 14 shows U937 cells treated with 10 nM of the compound the compound cholestane-3β,5α-diol-6β-N-[2-ethylamino(1H-imidazol-4-yl)] of example 9 for 24 hours. Photograph 1 corresponds to a "control" cell (magnification: 6000). Photograph 2 corresponds to a cell treated with the compound of example 9 (magnification: 4000): it is seen that the cell has changed shape and numerous intracytoplasmic vacuoles have appeared (referenced Vi in the photograph). The meanings of the reference letters in FIG. 14 are the same as those used for FIG. 11. In photograph 3 (magnification: 25 000), the presence of an extremely developed membrane network is observed; numerous cellular organites are distinguished (numerous mitochondria, which are evidence of intense activity); multivesicular bodies (MVB) are also distinguished, the detail of which appears in photograph 4 of FIG. 14, this photograph showing an MVB in the course of secretion out of the cell (magnification: 72 000).
Figure 14:
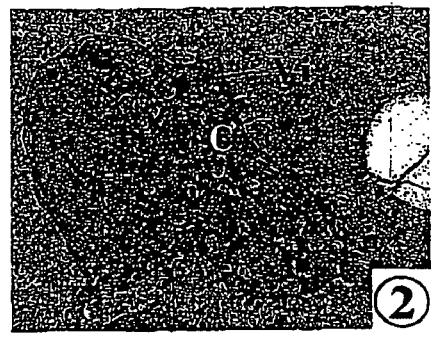
Figure 14:
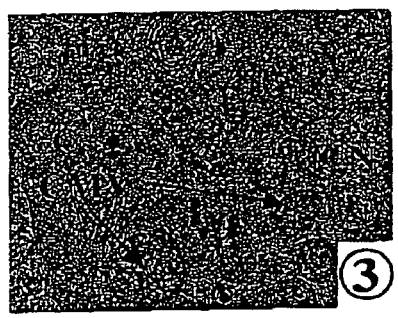
Figure 14:

The result is shown in FIG. 14. In this figure, photograph 1 corresponds to a "control" cell (magnification: 6000). Photograph 2 corresponds to a cell treated with the compound of example 9 (magnification: 4000): it is seen that the cell has changed shape and numerous intracytoplasmic vacuoles have appeared (referenced Vi in the photograph). The meanings of the reference letters in FIG. 14 are the same as those used for FIG. 11. In photograph 3 (magnification: 25 000), the presence of an extremely developed membrane network is observed; numerous cellular organites are distinguished (numerous mitochondria, which are evidence of intense activity); multivesicular bodies (MVB) are also distinguished, the detail of which appears in photograph 4 of FIG. 14, this photograph showing an MVB in the course of secretion out of the cell (magnification: 72 000).

The same observations were made when the compound of example 9 was replaced with the compound of one of the examples 46 and 47.

EXAMPLE 60

Overexpression of a Membrane Receptor in the U937 Tumoral Cell Line

U937 cells were cultured in an "RPMI 1640" medium sold by the company "Gibco BRL". A plasmid coding for an RCPG-MA membrane receptor belonging to the superfamily of protein G-coupled receptors and containing an HA label is generated.

The U937 cells expressing the receptors are generated by transfection using the "lipofectamine" reagent according to the manufacturer's instructions.

48 hours after transfection, the transfected cells were treated with 10 nM of compound according to example 9 for 12 hours.

Figure 15:
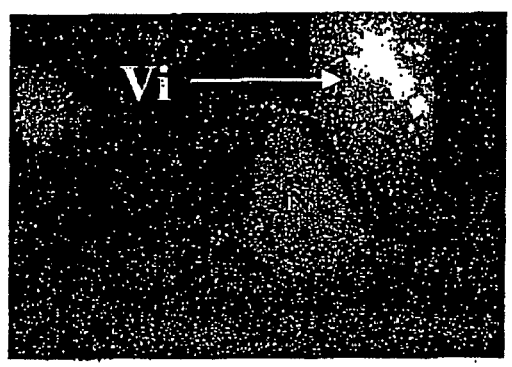
FIG. 15 shows two immunofluorescence photographs of U937 cells expressing RCPG-HA and which were subjected to a treatment with the compound cholestane-3β,5α-diol-6β-N-[2-ethylamino(1H-imidazol-4-yl)] of example 9. These cells were fixed in order to be examined by fluorescence microscopy. The photographs of FIG. 15 show the expression of a membrane receptor of RCPG type in the cells that were treated with the compound according to the invention, whereas in the absence of treatment, the immunodetection is difficult to achieve.
Figure 15:
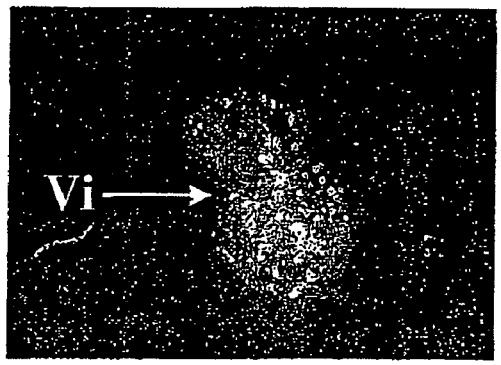

FIG. 15 shows two immunofluorescence photographs of U937 cells expressing RCPG-HA and which were subjected to a treatment with the compound of example 9. These cells were fixed in order to be examined by fluorescence microscopy. The presence of the receptor is revealed by incubation in the presence of an anti-HA antibody followed by incubation with an anti-IgG-FITC antibody. The photographs of FIG. 15 show the expression of a membrane receptor of RCPG type in the cells that were treated with the compound according to the invention, whereas in the absence of treatment, the immunodetection is difficult to achieve. The same observations are made when the compound of example 9 is replaced with the compound of one of the examples 10, 11, 14, 16, 46 and 47.

This experiment shows that the transfected cells can massively produce a membrane receptor in the intra-cytoplasmic vacuoles.

Examples 48 et seq, which have been described hereinabove, show that the cell types subjected to the experiments all produce vacuoles when they are treated with one of the compounds according to the invention: depending on the case, they may be multilamellar and/or multivesicular vacuoles. It is found that treatment with a compound according to the invention makes it possible to observe in the treated cells re-differentiation activity of the tumoral cells toward a normal phenotype.

The invention claimed is:

1. A sterol-based compound, corresponding to formula (I)

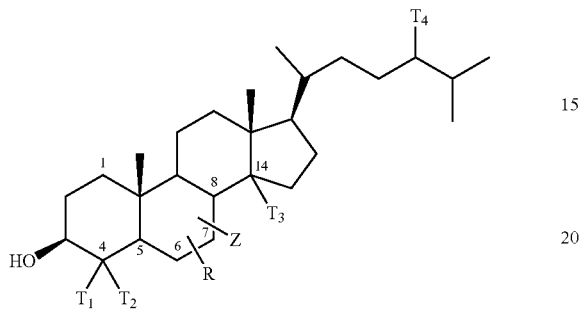

in which formula:
the carbon in position 4 of the cholesterol skeleton bears moieties $T_1$ and $T_2$, which are, independently, H or $CH_3$ with $CH_3$ in the $\alpha$ and/or $\beta$ position;
the carbon in position 24 bears a moiety $T_4$ which represents H, $CH_3$ or $C_2H_5$;
the carbon in position 14 bears a moiety $T_3$, which is H or a $\beta$ $CH_3$, the bond between carbons 7 and 8 is a single or a double bond;
Z represents, in position 5 or 8, either H or OH, H or OH being able to be borne only by a carbon that does not bear a double bond; and
R is in position 6 or 7, on a carbon not bearing a double bond,
said compound is selected from the group consisting of:
a compound corresponding to formula (I) in which the bond between carbons $C_7$ and $C_8$ is a double bond, R=NH—$(CH_2)_3$—NH—$(CH_2)_4$—$NH_2$ and $T_1=T_2=T_3$=H,
a compound corresponding to formula (I) in which the bond between carbons $C_7$ and $C_8$ is a double bond, $T_1=T_2=T_3$=H and

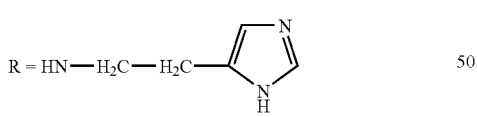

a compound corresponding to formula (I) in which the bond between carbons $C_7$ and $C_8$ is a double bond, $T_1=T_2=T_3$=H and R=—NH—$(CH_2)_4$—$NH_2$,
a compound corresponding to formula (I) in which the bond $C_7$-$C_8$ is a double bond, $T_1=T_2=T_3$=H and R=—NH—$(CH_2)_2$—O—$(CH_2)_2$—O—$(CH_2)_2$—$NH_2$,
a compound corresponding to formula (I) in which the bond $C_7$-$C_8$ is a single bond, Z represents OH in position 5 and $T_1=T_2=T_3$=H, R being in position 6, and R=—NH—$(CH_2)_3$—NH—$(CH_2)_4$—NH—$(CH_2)_3$—$NH_2$,
a compound corresponding to formula (I) in which the bond $C_7$-$C_8$ is a single bond, Z represents OH in position 5 and $T_1=T_2=T_3$=H, R being in position 6, and

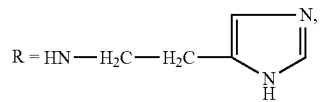

a compound corresponding to formula (I) in which the bond $C_7$-$C_8$ is a single bond, Z represents OH in position 5 and $T_1=T_2=T_3$=H, R being in position 6 and having the meaning

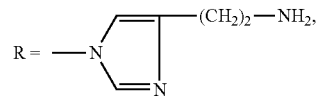

a compound corresponding to formula (I) in which the bond $C_7$-$C_8$ is a single bond, Z represents OH in position 5 and $T_1=T_2=T_3$=H, R being in position 6 and having the meaning

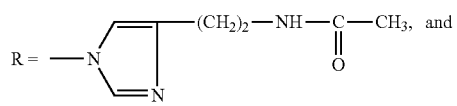

a compound corresponding to formula (I) in which the bond $C_7$-$C_8$ is a single bond, Z represents OH in position 5 and $T_1=T_2=T_3$=H, R being in position 6 and being: NH—$(CH_2)_3$—NH—$(CH_2)_4$—$NH_2$.

2. A medicament, comprising, in a pharmaceutically acceptable vehicle, at least one compound as claimed in claim 1.

3. The medicament as claimed in claim 2, wherein the pharmaceutically acceptable vehicle is a vehicle for administration by injection.

4. A process for preparing a compound as claimed in claim 1, comprising:
in a first step, reacting meta-chloroperoxybenzoic acid, dissolved in methylene chloride, with a compound corresponding to formula (III)

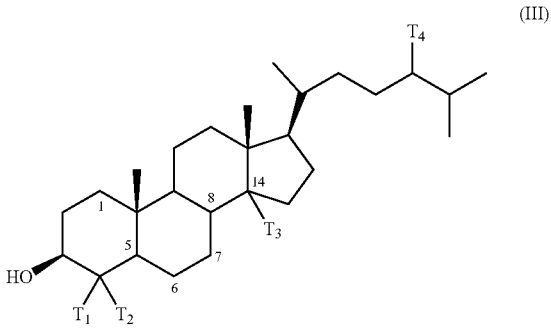

in which formula the carbon in position 4 of the cholesterol skeleton bears moieties $T_1$ and $T_2$ which is, independently, H or $CH_3$ with $CH_3$ in the $\alpha$ and/or $\beta$ position, the carbon in position 24 bears a moiety $T_4$ that represents H, $CH_3$ or $C_2H_5$, the carbon in position 14 bears a moiety $T_3$, which is H or a $\beta$ $CH_3$, the bond between carbons 5 and 6 is a double bond, and the compound of formula III being dissolved in a solvent selected from group consisting of methylene chloride, a mixture of methylene chloride with water and a mixture of methylene chloride and aqueous $Na_2CO_3$ solution; and in a second step, reacting the epoxy compound obtained in the first step, dissolved in a solvent selected from the group consisting of an ethanolic solution, anhydrous ethanol and pyridine in the presence of lithium perchlorate, with an amine, dissolved in anhydrous ethanol, the amine being selected from the group consisting of:

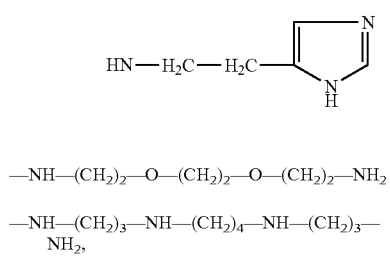

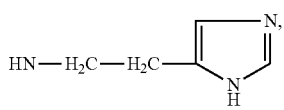

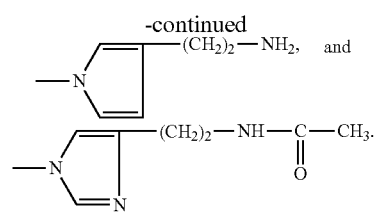

5. The process as claimed in claim 4, wherein the product obtained in the first step is purified before using it for the second step.

6. The process as claimed in claim 4, for the preparation of a compound of formula (I) bearing an OH on the carbon in position 5 and comprising a double bond between carbons 7 and 8, wherein compound (III) of formula is dissolved in a mixture of methylene chloride and of aqueous $Na_2CO_3$ solution.

7. The process as claimed in claim 4, for the preparation of a compound of formula (I) bearing an OH on the carbon in position 5 and comprising a single bond between carbons 7 and 8, wherein compound of formula (III) is dissolved in methylene chloride.

8. The process as claimed in claim 6, wherein the reaction of the second step is performed at reflux, at atmospheric pressure.

* * * * *